United States Patent
Suzuki et al.

(10) Patent No.: US 11,986,546 B2
(45) Date of Patent: May 21, 2024

(54) DEXTRIN FATTY ACID ESTER AND COSMETIC

(71) Applicant: CHIBA FLOUR MILLING CO., LTD., Chiba (JP)

(72) Inventors: Takanao Suzuki, Chiba (JP); Daisuke Kato, Chiba (JP)

(73) Assignee: CHIBA FLOUR MILLING CO., LTD., Chiba (JP)

(*) Notice: Subject to any disclaimer, the term of this patent is extended or adjusted under 35 U.S.C. 154(b) by 0 days.

(21) Appl. No.: 16/781,383

(22) Filed: Feb. 4, 2020

(65) Prior Publication Data
US 2020/0170917 A1 Jun. 4, 2020

Related U.S. Application Data

(62) Division of application No. 15/566,080, filed as application No. PCT/JP2016/061826 on Apr. 12, 2016, now abandoned.

(30) Foreign Application Priority Data

Apr. 13, 2015 (JP) ................................. 2015-081477

(51) Int. Cl.
| A61K 8/73 | (2006.01) |
| A61K 8/31 | (2006.01) |
| A61Q 1/02 | (2006.01) |
| A61Q 1/04 | (2006.01) |
| A61Q 1/08 | (2006.01) |
| A61Q 1/10 | (2006.01) |
| A61Q 5/00 | (2006.01) |
| A61Q 19/00 | (2006.01) |
| A61Q 19/10 | (2006.01) |
| C07H 13/06 | (2006.01) |
| C08B 30/18 | (2006.01) |

(52) U.S. Cl.
CPC .................. *A61K 8/73* (2013.01); *A61K 8/31* (2013.01); *A61Q 1/02* (2013.01); *A61Q 1/04* (2013.01); *A61Q 1/08* (2013.01); *A61Q 1/10* (2013.01); *A61Q 5/00* (2013.01); *A61Q 19/00* (2013.01); *A61Q 19/10* (2013.01); *C07H 13/06* (2013.01); *C08B 30/18* (2013.01)

(58) Field of Classification Search
None
See application file for complete search history.

(56) References Cited

U.S. PATENT DOCUMENTS 5,840,883 A * 11/1998 Suzuki .................. A61Q 19/00
536/110

FOREIGN PATENT DOCUMENTS

| EP | 1386600 A1 * | 2/2004 | ............ A61K 8/042 |
| JP | H08277302 A | 10/1996 | |
| JP | 3019191 B2 | 1/2000 | |
| JP | 2000072646 A | 3/2000 | |
| JP | 2005145851 A | 6/2005 | |
| JP | 2011213662 A | 10/2011 | |
| JP | 2011225562 A | 11/2011 | |
| JP | 2012201663 A | 10/2012 | |
| JP | 2014196263 A | 10/2014 | |
| JP | 2014196263 A1 | 10/2014 | |
| JP | 2016199698 A | 12/2016 | |
| WO | 2016167255 A1 | 10/2016 | |

OTHER PUBLICATIONS

Youriko (JP2014-196263, wherein a machine translation is provided) (Year: 2014).*
Daisuke et al (JP2005145851; wherein a machine translation is proved) (Year: 2005).*
International Search Report (ISA/JP); PCT/JP2016/061826; completion date of ISR May 13, 2016 (2 pages).
Office Action dated Oct. 10, 2017, was received during the prosecution of the related Japanese patent application JP 2016-199698 (4 pages).
Translation-Notification of Reasons for Refusal, date of drafting Sep. 29, 2017, 5 pages.
Translation of "International Preliminary Report on Patentability", dated Nov. 6, 2017, International Application No. PCT/JP2016/061826, pp. 1-6.
JP2014-196263, machine translation (Year: 2014), 26 pages.
Office Action (including machine translation of Office Action) drafted Sep. 29, 2017, received during the prosecution of the related Japanese patent application JP 2017-139865; 9 pages.

* cited by examiner

*Primary Examiner* — Jake M Vu
(74) *Attorney, Agent, or Firm* — CANTOR COLBURN LLP

(57) ABSTRACT

A dextrin fatty acid ester is provided in which the dextrin has an average degree of glycopolymerization of 3 or more and 100 or less. The fatty acid comprises one or more linear saturated fatty acids having 14 or more and 18 or less carbon atoms, and one or more branched saturated fatty acids having 14 or more and 18 or less carbon atoms. The molar fraction of the linear saturated fatty acid in the fatty acid is 0.75 or more and 0.95 or less. The average degree of substitution of the fatty acid per glucose unit is 1.5 or more and 2.0 or less.

7 Claims, 14 Drawing Sheets

Fig.1

| | Average degree of glycopolymerization | Dextrin weight (g) | Reaction system | | | | Linear saturated fatty acid | | Branched saturated fatty acid | |
|---|---|---|---|---|---|---|---|---|---|---|
| | | | Solvent | Solvent weight (g) | Catalyst | Catalyst weight (g) | Fatty acid | Weight (g) | Fatty acid | Weight (g) |
| Example 1 | 20 | 73 | DMF | 219 | Pyridine | 99 | Palmitic acid | 223 | 2-Hexyldecanoic acid | 52 |
| Example 2 | 3 | 72 | Hep | 72 | Picoline | 116 | Myristic acid | 207 | Isostearic acid (Emery method) | 48 |
| Example 3 | 50 | 68 | NMP | 135 | Picoline | 116 | Stearic acid | 206 | 12-Methyltridecanoic acid | 79 |
| Example 4 | 20 | 77 | DMF | 193 | Picoline | 116 | Palmitic acid | 253 | Isostearic acid (Guerbet reaction) | 24 |
| Example 5 | 20 | 70 | DMF | 211 | Picoline | 116 | Myristic acid/ palmitic acid | 93/103 | 2-Hexyldecanoic acid | 69 |
| Example 6 | 10 | 74 | DMF | 221 | Picoline | 116 | Palmitic acid | 237 | 2-Hexyldecanoic acid | 39 |
| Comparative Example 1 | 2 | 74 | DMF | 221 | Picoline | 116 | Palmitic acid | 220 | 2-Hexyldecanoic acid | 55 |
| Comparative Example 2 | 20 | 77 | DMF | 232 | Picoline | 116 | Palmitic acid | 275 | — | 0 |
| Comparative Example 3 | 20 | 77 | DMF | 232 | Picoline | 116 | Palmitic acid | 206 | 2-Ethylhexanoic acid | 41 |
| Comparative Example 4 | 20 | 56 | DMF | 168 | Picoline | 116 | Palmitic acid | 217 | 2-Hexyldecanoic acid | 58 |
| Comparative Example 5 | 20 | 81 | DMF | 243 | Picoline | 116 | Palmitic acid | 231 | 2-Hexyldecanoic acid | 44 |
| Comparative Example 6 | 20 | 72 | DMF | 216 | Picoline | 116 | Lauric acid | 184 | 2-Hexyldecanoic acid | 44 |
| Comparative Example 7 | 20 | 52 | DMF | 157 | Picoline | 116 | Palmitic acid | 275 | — | 0 |
| Comparative Example 8 | 20 | 60 | DMF | 180 | Picoline | 116 | Palmitic acid | 165 | 2-Hexyldecanoic acid | 110 |
| Comparative Example 9 | 20 | 66 | DMF | 199 | Picoline | 116 | Myristic acid | 161 | 2-Hexyldecanoic acid | 36 |

Fig.2

|  | Synthesized product | | | |
| --- | --- | --- | --- | --- |
|  | Mole of linear form (%) | Mole of branched form (%) | Average degree of substitution | Yield (g) |
| Example1 | 85 | 15 | 1.67 | 220 |
| Example2 | 88 | 12 | 1.73 | 205 |
| Example3 | 75 | 25 | 1.99 | 251 |
| Example4 | 95 | 5 | 1.52 | 203 |
| Example5 | 80 | 20 | 1.80 | 192 |
| Example6 | 90 | 10 | 1.61 | 211 |
| Comparative Example1 | 83 | 17 | 1.80 | 230 |
| Comparative Example2 | 100 | 0 | 1.50 | 205 |
| Comparative Example3 | 87 | 13 | 1.50 | 185 |
| Comparative Example4 | 83 | 17 | 2.06 | 201 |
| Comparative Example5 | 87 | 13 | 1.43 | 189 |
| Comparative Example6 | 88 | 12 | 1.62 | 169 |
| Comparative Example7 | 100 | 0 | 2.20 | 190 |
| Comparative Example8 | 63 | 37 | 1.90 | 172 |
| Comparative Example9 | 70 | 30 | 1.70 | 171 |

Fig.3

|  | Mineral oil | | Isododecane | |
| --- | --- | --- | --- | --- |
|  | Concentration (%) | Initial viscosity (Pa·s) | Concentration (%) | Initial viscosity (Pa·s) |
| Example1 | 7 | 45 | 12 | 123 |
| Example2 | 6 | 41 | 10 | 111 |
| Example3 | 8 | 52 | 12 | 130 |
| Example4 | 8 | 46 | 12 | 122 |
| Example5 | 9 | 50 | 12 | 135 |
| Example6 | 7 | 41 | 10 | 140 |
| Comparative Example1 | 7 | 44 | 12 | 121 |
| Comparative Example2 | 7 | 42 | 14 | 139 |
| Comparative Example3 | 8 | 40 | 15 | 191 |
| Comparative Example4 | 6 | 47 | 12 | 180 |
| Comparative Example5 | 8 | 49 | 15 | 174 |
| Comparative Example6 | 8 | 40 | 16 | 185 |
| Comparative Example7 | 5 | 47 | 9 | 150 |
| Comparative Example8 | 12 | 58 | 30 | - |
| Comparative Example9 | 11 | 55 | 24 | - |

Fig.5

| | Mineral oil | | | | | Isododecane | | | | |
|---|---|---|---|---|---|---|---|---|---|---|
| | Restoring force | Syneresis properties | Viscosity | Transparency | Dissolution temperature | Restoring force | Syneresis properties | Viscosity | Transparency | Dissolution temperature |
| Example1 | ◎ | ◎ | ◎ | ◎ | ◎ | ◎ | ◎ | ◎ | ◎ | ◎ |
| Example2 | ◎ | ○ | ◎ | ◎ | ◎ | ◎ | ○ | ○ | ◎ | ◎ |
| Example3 | ◎ | ○ | ◎ | ◎ | ○ | ○ | ○ | ○ | ◎ | ○ |
| Example4 | ○ | ○ | ○ | ◎ | ○ | ◎ | ○ | ○ | ◎ | ○ |
| Example5 | ◎ | ◎ | ◎ | ◎ | ◎ | ◎ | ◎ | ◎ | ◎ | ◎ |
| Example6 | ◎ | ◎ | ◎ | ◎ | ◎ | ◎ | ◎ | ◎ | ○ | ◎ |
| Comparative Example1 | ○ | × | × | ○ | ◎ | ○ | × | × | ○ | ◎ |
| Comparative Example2 | ○ | × | ○ | × | ○ | × | × | ○ | × | ○ |
| Comparative Example3 | × | ○ | × | ◎ | ○ | × | ○ | × | ◎ | ◎ |
| Comparative Example4 | ○ | × | ○ | × | × | ○ | × | ○ | × | × |
| Comparative Example5 | × | × | × | × | ○ | × | × | × | × | ○ |
| Comparative Example6 | ○ | × | ○ | ○ | ○ | ○ | × | ○ | ◎ | ○ |
| Comparative Example7 | ◎ | × | ○ | × | ◎ | ◎ | × | ◎ | × | ◎ |
| Comparative Example8 | × | ◎ | × | ◎ | ◎ | × | ◎ | × | × | ◎ |
| Comparative Example9 | × | ◎ | × | ◎ | ◎ | × | ◎ | × | ◎ | ◎ |

Fig.6

<Mascara>

| | Example A1 | Example A2 | Example A3 | Comparative Example A1 | Comparative Example A2 | Comparative Example A3 | Comparative Example A4 | Comparative Example A5 |
|---|---|---|---|---|---|---|---|---|
| | Example1 | Example3 | Example4 | Comparative Example2 | Comparative Example3 | Comparative Example7 | Comparative Example6 | Comparative Example9 |
| Dextrin fatty acid ester | 10 | 10 | 10 | 10 | 10 | 8 | 20 | 15 |
| Dextrin fatty acid ester (proportion) | 40 | 40 | 40 | 40 | 40 | 42 | 30 | 35 |
| Isododecane | 5 | 5 | 5 | 5 | 5 | 5 | 5 | 5 |
| Polyethylene | 1 | 1 | 1 | 1 | 1 | 1 | 1 | 1 |
| Microcrystalline wax | 1 | 1 | 1 | 1 | 1 | 1 | 1 | 1 |
| Candelilla wax | 16.8 | 16.8 | 16.8 | 16.8 | 16.8 | 16.8 | 16.8 | 16.8 |
| Trimethylsiloxysilicic acid | 11.2 | 11.2 | 11.2 | 11.2 | 11.2 | 11.2 | 11.2 | 11.2 |
| Isododecane | 5 | 5 | 5 | 5 | 5 | 5 | 5 | 5 |
| Iron oxide black | 6 | 6 | 6 | 6 | 6 | 6 | 6 | 6 |
| Talc | 4 | 4 | 4 | 4 | 4 | 4 | 4 | 4 |
| Nylon-12 | 100 | 100 | 100 | 100 | 100 | 100 | 100 | 100 |
| Total (%) | ◎ | ◎ | ◎ | × | ○ | △ | △ | △ |
| Preservation stability | ◎ | ◎ | ◎ | ○ | ○ | △ | ○ | ○ |
| Adhesion to brush | ◎ | ◎ | ◎ | ◎ | ◎ | ○ | ◎ | ◎ |
| Makeup effect/gloss | ◎ | ○ | ◎ | ○ | ○ | ○ | ○ | ○ |
| Spread upon application | ◎ | ◎ | ◎ | ◎ | △ | ◎ | △ | △ |
| Volume-up effect | ◎ | ◎ | ◎ | ◎ | ◎ | ◎ | △ | △ |
| Separation effect | | | | | | | | |
| Rub resistance | | | | | | | | |

Fig. 7

<Body oil>

| | Example B1 | Example B2 | Example B3 | Comparative Example B1 | Comparative Example B2 | Comparative Example B3 | Comparative Example B4 | Comparative Example B5 |
|---|---|---|---|---|---|---|---|---|
| | Example1 | Example3 | Example4 | Comparative Example2 | Comparative Example3 | Comparative Example7 | Comparative Example8 | Comparative Example9 |
| Dextrin fatty acid ester | | | | | | | | |
| Dextrin fatty acid ester (proportion) | 2 | 2 | 2 | 2 | 4 | 1.2 | 6 | 6 |
| Squalane | 27.5 | 27.5 | 27.5 | 27.5 | 25.5 | 28.3 | 23.5 | 23.5 |
| Octyldodecyl myristate | 23 | 23 | 23 | 23 | 23 | 23 | 23 | 23 |
| Isotridecyl isononanoate | 19.46 | 19.46 | 19.46 | 19.46 | 19.46 | 19.46 | 19.46 | 19.46 |
| Cetyl ethylhexanoate | 16 | 16 | 16 | 16 | 16 | 16 | 16 | 16 |
| Trioctanoin | 12 | 12 | 12 | 12 | 12 | 12 | 12 | 12 |
| Tocopherol | 0.04 | 0.04 | 0.04 | 0.04 | 0.04 | 0.04 | 0.04 | 0.04 |
| Total (%) | 100 | 100 | 100 | 100 | 100 | 100 | 100 | 100 |
| Preservation stability | ◎ | ◎ | ◎ | ◎ | ○ | △ | △ | △ |
| Absence of dropping | ◎ | ◎ | ◎ | ○ | ○ | △ | △ | △ |
| Spread | ◎ | ◎ | ◎ | ◎ | ◎ | ○ | △ | △ |
| Impression from use | ◎ | ◎ | ◎ | ○ | ○ | △ | △ | △ |
| Transparency | ◎ | ◎ | ◎ | △ | ◎ | △ | ◎ | ◎ |

Fig.8

<Cleansing gel>

| | Example C1 | Example C2 | Example C3 | Comparative Example C1 | Comparative Example C2 | Comparative Example C3 | Comparative Example C4 | Comparative Example C5 |
|---|---|---|---|---|---|---|---|---|
| | Example1 | Example3 | Example4 | Comparative Example2 | Comparative Example3 | Comparative Example7 | Comparative Example8 | Comparative Example9 |
| Dextrin fatty acid ester | | | | | | | | |
| Dextrin fatty acid ester (proportion) | 3 | 3 | 3 | 3 | 8 | 2 | 10 | 10 |
| Mineral oil | 29 | 29 | 29 | 29 | 24 | 30 | 22 | 22 |
| Isotridecyl isononanoate | 16 | 16 | 16 | 16 | 16 | 16 | 16 | 16 |
| Squalane | 8 | 8 | 8 | 8 | 8 | 8 | 8 | 8 |
| Octyldodecanol | 16 | 16 | 16 | 16 | 16 | 16 | 16 | 16 |
| Trioctanoin | 8 | 8 | 8 | 8 | 8 | 8 | 8 | 8 |
| Sorbeth-40 tetraoleate | 16 | 16 | 16 | 16 | 16 | 16 | 16 | 16 |
| Water | 4 | 4 | 4 | 4 | 4 | 4 | 4 | 4 |
| Total (%) | 100 | 100 | 100 | 100 | 100 | 100 | 100 | 100 |
| Preservation stability | ◎ | ◎ | ◎ | ◎ | ○ | △ | △ | △ |
| Transparency | ◎ | ◎ | ◎ | ○ | ◎ | × | ◎ | ◎ |
| Absence of dropping | ◎ | ◎ | ◎ | ◎ | ○ | △ | △ | △ |
| Spread | ◎ | ◎ | ◎ | ◎ | ◎ | × | △ | △ |
| Impression from use | ◎ | ◎ | ◎ | ○ | ○ | △ | △ | △ |

Fig.9

<Hair treatment gel>

| | Example D1 | Example D2 | Example D3 | Comparative Example D1 | Comparative Example D2 | Comparative Example D3 | Comparative Example D4 | Comparative Example D5 |
|---|---|---|---|---|---|---|---|---|
| Dextrin fatty acid ester | Example1 | Example3 | Example4 | Comparative Example2 | Comparative Example3 | Comparative Example7 | Comparative Example8 | Comparative Example9 |
| Dextrin fatty acid ester (proportion) | 4 | 4 | 4 | 4 | 8 | 2 | 10 | 10 |
| Olefin oligomer | 43 | 43 | 43 | 43 | 39 | 45 | 37 | 37 |
| Isononyl isononanoate | 32 | 32 | 32 | 32 | 32 | 32 | 32 | 32 |
| Octyldodecanol | 10 | 10 | 10 | 10 | 10 | 10 | 10 | 10 |
| Di(phytosteryl/octyldodecyl) lauroyl glutamate | 6 | 6 | 6 | 6 | 6 | 6 | 6 | 6 |
| Isostearoyl hydrolyzed silk, isostearic acid | 5 | 5 | 5 | 5 | 5 | 5 | 5 | 5 |
| Total (%) | 100 | 100 | 100 | 100 | 100 | 100 | 100 | 100 |
| Preservation stability | ◎ | ◎ | ◎ | × | ○ | △ | △ | △ |
| Transparency | ○ | ○ | ○ | △ | ○ | × | ○ | ○ |
| Absence of dropping | ◎ | ◎ | ◎ | △ | △ | ○ | △ | △ |
| Spread | ◎ | ◎ | ◎ | ○ | ○ | △ | △ | △ |
| Impression from use | ◎ | ◎ | ◎ | ○ | ○ | △ | △ | △ |

Fig.10

<Lip color>

| | Example E1 | Example E2 | Example E3 | Comparative Example E1 | Comparative Example E2 | Comparative Example E3 | Comparative Example E4 | Comparative Example E5 |
|---|---|---|---|---|---|---|---|---|
| Dextrin fatty acid ester | Example1 | Example3 | Example4 | Example2 | Example3 | Example7 | Example8 | Example9 |
| Dextrin fatty acid ester (proportion) | 5 | 5 | 5 | 5 | 8 | 2.5 | 10 | 10 |
| Trioctanoin | 23 | 23 | 23 | 23 | 20 | 25.5 | 13 | 13 |
| Dimethicone copolyol | 1.6 | 1.6 | 1.6 | 1.6 | 1.6 | 1.6 | 1.6 | 1.6 |
| Cyclomethicone | 44.4 | 44.4 | 44.4 | 44.4 | 44.4 | 44.4 | 44.4 | 44.4 |
| Butylene glycol | 5 | 5 | 5 | 5 | 5 | 5 | 5 | 5 |
| Water | 21 | 21 | 21 | 21 | 21 | 21 | 21 | 21 |
| Pigment | q.s. | q.s. | q.s. | q.s. | q.s. | q.s. | q.s. | q.s. |
| Total (%) | 100 | 100 | 100 | 100 | 100 | 100 | 100 | 100 |
| Preservation stability | ◎ | ◎ | ◎ | ◎ | ○ | ○ | △ | △ |
| Ease to take out using applicator | ◎ | ◎ | ◎ | ○ | ○ | △ | △ | △ |
| Spread upon use | ◎ | ◎ | ◎ | ○ | ○ | △ | △ | △ |
| Smudge resistance | ◎ | ◎ | ◎ | ○ | △ | ○ | × | × |

Fig.11
<Lip gloss>

| | Example F1 | Example F2 | Example F3 | Comparative Example F1 | Comparative Example F2 | Comparative Example F3 | Comparative Example F4 | Comparative Example F5 |
|---|---|---|---|---|---|---|---|---|
| | Example1 | Example3 | Example4 | Comparative Example2 | Comparative Example3 | Comparative Example7 | Comparative Example8 | Comparative Example9 |
| Dextrin fatty acid ester | 5 | 5 | 5 | 5 | 8 | 3 | 10 | 10 |
| Dextrin fatty acid ester (proportion) | 24 | 24 | 24 | 24 | 21 | 26 | 19 | 19 |
| Mineral oil | 14 | 14 | 14 | 14 | 14 | 14 | 14 | 14 |
| Pentaerythrityl hydrogenatedrosinate, octyldodecyl isostearate | 10 | 10 | 10 | 10 | 10 | 10 | 10 | 10 |
| Diisostearyl malate | 7 | 7 | 7 | 7 | 7 | 7 | 7 | 7 |
| Diphenylsiloxy phenyl trimethicone | 40 | 40 | 40 | 40 | 40 | 40 | 40 | 40 |
| Hydrogenated polyisobutene | q.s. | q.s. | q.s. | q.s. | q.s. | q.s. | q.s. | q.s. |
| Pigment | 100 | 100 | 100 | 100 | 100 | 100 | 100 | 100 |
| Total (%) | ◎ | ◎ | ◎ | △ | △ | △ | △ | △ |
| Preservation stability | ◎ | ◎ | ◎ | ○ | ○ | △ | △ | △ |
| Ease to take out using applicator | ◎ | ◎ | ◎ | ○ | ○ | △ | △ | △ |
| Spread upon use | ◎ | ◎ | ◎ | ○ | ○ | ○ | △ | △ |
| Smudge resistance | | | | | | | | |

Fig.12
<Oil foundation>

| | Example G1 | Example G2 | Example G3 | Comparative Example G1 | Comparative Example G2 | Comparative Example G3 | Comparative Example G4 | Comparative Example G5 |
|---|---|---|---|---|---|---|---|---|
| Dextrin fatty acid ester | Example1 | Example3 | Example4 | Comparative Example2 | Comparative Example3 | Comparative Example7 | Comparative Example8 | Comparative Example9 |
| Dextrin fatty acid ester (proportion) | 4 | 4 | 4 | 4 | 8 | 2 | 10 | 10 |
| Mineral oil | 16 | 16 | 16 | 16 | 12 | 18 | 10 | 10 |
| Isotridecyl isononanoate | 16 | 16 | 16 | 16 | 16 | 16 | 16 | 16 |
| Squalane | 16 | 16 | 16 | 16 | 16 | 16 | 16 | 16 |
| Diphenylsiloxy phenyl trimethicone | 16 | 16 | 16 | 16 | 16 | 16 | 16 | 16 |
| Isododecane | 32 | 32 | 32 | 32 | 32 | 32 | 32 | 32 |
| Pigment | q.s. | q.s. | q.s. | q.s. | q.s. | q.s. | q.s. | q.s. |
| Total (%) | 100 | 100 | 100 | 100 | 100 | 100 | 100 | 100 |
| Preservation stability | ◎ | ◎ | ◎ | △ | △ | △ | △ | △ |
| Absence of dropping | ◎ | ◎ | ◎ | ○ | ○ | △ | △ | △ |
| Long-lasting makeup | ◎ | ◎ | ◎ | ◎ | ◎ | ○ | △ | △ |
| Impression from use | ◎ | ◎ | ◎ | ○ | ○ | △ | △ | △ |

Fig.13
<Beauty oil>

| | Example H1 Example1 | Example H2 Example3 | Example H3 Example4 | Comparative Example H1 Comparative Example2 | Comparative Example H2 Comparative Example3 | Comparative Example H3 Comparative Example7 | Comparative Example H4 Comparative Example8 | Comparative Example H5 Comparative Example9 |
|---|---|---|---|---|---|---|---|---|
| Dextrin fatty acid ester | 1.5 | 1.5 | 1.5 | 1.5 | 3 | 1 | 4.5 | 4.5 |
| Dextrin fatty acid ester (proportion) | 1 | 1 | 1 | 1 | 1 | 1 | 1 | 1 |
| Coix lacryma-jobi ma-yuen seed oil | 20 | 20 | 20 | 20 | 18.5 | 19.5 | 17 | 17 |
| Isotridecyl isononanoate | 18 | 18 | 18 | 18 | 18 | 18 | 18 | 18 |
| Jojoba oil | 16 | 16 | 16 | 16 | 16 | 16 | 16 | 16 |
| Trioctanoin | 16.45 | 16.45 | 16.45 | 16.45 | 16.45 | 16.45 | 16.45 | 16.45 |
| Mineral oil | 12 | 12 | 12 | 12 | 12 | 12 | 12 | 12 |
| Squalane | 9 | 9 | 9 | 9 | 9 | 9 | 9 | 9 |
| Olive oil | 6 | 6 | 6 | 6 | 6 | 6 | 6 | 6 |
| Avocado oil | 0.05 | 0.05 | 0.05 | 0.05 | 0.05 | 0.05 | 0.05 | 0.05 |
| Tocopherol | | | | | | | | |
| Total (%) | 100 | 100 | 100 | 100 | 100 | 100 | 100 | 100 |
| Preservation stability | ◎ | ◎ | ◎ | ○ | ○ | △ | △ | △ |
| Transparency | ○ | ○ | ○ | △ | ○ | × | ○ | ○ |
| Absence of dropping | ◎ | ◎ | ◎ | ○ | △ | ○ | △ | △ |
| Spread | ◎ | ◎ | ◎ | ○ | ○ | △ | △ | △ |
| Impression from use | ◎ | ◎ | ◎ | ○ | ○ | △ | △ | △ |

Fig.14
<Liquid rouge>

| | Example J1 Example1 | Example J2 Example3 | Example J3 Example4 | Comparative Example J1 Comparative Example2 | Comparative Example J2 Comparative Example3 | Comparative Example J3 Comparative Example7 | Comparative Example J4 Comparative Example8 | Comparative Example J5 Comparative Example9 |
|---|---|---|---|---|---|---|---|---|
| Dextrin fatty acid ester (proportion) | 15 | 15 | 15 | 15 | 18 | 10 | 20 | 20 |
| Dextrin isostearate | 10 | 10 | 10 | 10 | 10 | 10 | 10 | 10 |
| Diisostearyl malate | 22 | 22 | 22 | 22 | 22 | 22 | 22 | 22 |
| Isododecane | 33.5 | 33.5 | 33.5 | 33.5 | 30.5 | 38.5 | 28.5 | 28.5 |
| Hydrogenated polyisobutene | 4 | 4 | 4 | 4 | 4 | 4 | 4 | 4 |
| Silica | 5 | 5 | 5 | 5 | 5 | 5 | 5 | 5 |
| Mica | 6 | 6 | 6 | 6 | 6 | 6 | 6 | 6 |
| Pearl agent | 2 | 2 | 2 | 2 | 2 | 2 | 2 | 2 |
| Pigment | 2.5 | 2.5 | 2.5 | 2.5 | 2.5 | 2.5 | 2.5 | 2.5 |
| Total (%) | 100 | 100 | 100 | 100 | 100 | 100 | 100 | 100 |
| Preservation stability | ◎ | ◎ | ◎ | ◎ | ○ | △ | △ | △ |
| Ease to take out using applicator | ◎ | ◎ | ◎ | ○ | ○ | △ | △ | △ |
| Spread upon use | ◎ | ◎ | ◎ | ○ | ○ | △ | △ | △ |
| Smudge resistance | ◎ | ◎ | ◎ | ○ | △ | ○ | × | × |

Fig. 15

<Gel eyeliner>

| | Example K1 | Example K2 | Example K3 | Comparative Example K1 | Comparative Example K2 | Comparative Example K3 | Comparative Example K4 | Comparative Example K5 |
|---|---|---|---|---|---|---|---|---|
| | Example1 | Example3 | Example4 | Comparative Example2 | Comparative Example3 | Comparative Example7 | Comparative Example8 | Comparative Example9 |
| Dextrin fatty acid ester (proportion) | 3.5 | 3.5 | 3.5 | 3.5 | 4.5 | 3 | 6.5 | 6.5 |
| Dextrin fatty acid ester | 6 | 6 | 6 | 6 | 6 | 6 | 6 | 6 |
| Polyethylene | 2 | 2 | 2 | 2 | 2 | 2 | 2 | 2 |
| Microcrystalline wax | 49.5 | 49.5 | 49.5 | 49.5 | 49.5 | 49 | 46.5 | 46.5 |
| Light liquid isoparaffin | 23 | 23 | 23 | 23 | 22 | 23 | 23 | 23 |
| Decamethylcyclopentasiloxane | 6 | 6 | 6 | 6 | 6 | 6 | 6 | 6 |
| Polymethylsilsesquioxane | 6 | 6 | 6 | 6 | 6 | 6 | 6 | 6 |
| Trimethylsiloxysilicic acid | 4 | 4 | 4 | 4 | 4 | 4 | 4 | 4 |
| Isododecane | | | | | | | | |
| Pigment | q.s. | q.s. | q.s. | q.s. | q.s. | q.s. | q.s. | q.s. |
| Total (%) | 100 | 100 | 100 | 100 | 100 | 100 | 100 | 100 |
| Preservation stability | ◎ | ◎ | ◎ | ◎ | ○ | ○ | △ | △ |
| Absence of dropping | ◎ | ◎ | ◎ | ○ | ○ | △ | △ | △ |
| Spread upon use | ◎ | ◎ | ◎ | ○ | ○ | △ | △ | △ |
| Smudge resistance | ◎ | ◎ | ◎ | ○ | △ | ○ | × | × |

DEXTRIN FATTY ACID ESTER AND COSMETIC

DOMESTIC PRIORITY

This application is a Divisional of U.S. patent application Ser. No. 15/566,080 entitled "Dextrin Fatty Acid Ester and Cosmetic," filed Oct. 12, 2017 which is a national stage of International Application No. PCT/JP2016/061826, filed Apr. 12, 2016, which claims priority to Japanese Patent Application No. 2015-081477, filed Apr. 13, 2015, the contents of which are incorporated herein by reference in their entireties.

TECHNICAL FIELD

The present invention relates to a dextrin fatty acid ester and a cosmetic containing the dextrin fatty acid ester.

BACKGROUND ART

Dextrin fatty acid esters have heretofore been used as gelling agents, which gel oils. The oils gelled by the dextrin fatty acid esters are excellent in transparency, gloss, texture, etc. and are therefore used as materials for cosmetics.

For cosmetics, thixotropy is one of the important performances. The thixotropy is a performance by which a substance reduces its viscosity by the application of a given force and restores the viscosity without the force. Cosmetics having high thixotropy exert effects, for example, good spreadability, because their viscosities are reduced upon application of the cosmetics. After the application of the cosmetics, the cosmetics resist flowing down and easily maintain the state of completion of application of the cosmetics, because the cosmetics restore their viscosities.

Patent Document 1 describes a dextrin fatty acid ester that imparts high thixotropy to a cosmetic and use of this dextrin fatty acid ester in a cosmetic.

PRIOR ART DOCUMENT

Patent Document
Patent Document 1: Japanese Patent No. 3019191

SUMMARY OF THE INVENTION

Problems that the Invention is to Solve

The number of types of cosmetics comprising dextrin fatty acid esters keeps increasing. Along with this, new physical properties are required for the dextrin fatty acid esters. Specifically, high thixotropy may be imparted to cosmetics by the dextrin fatty acid esters. Even in such a case, cosmetics such as body oils or hair treatment gels can be poorly practical. That is, depending on a condition where the cosmetics are used, the cosmetics taken up on the palm or put on the skin excessively flow down if a long time is required for the cosmetics to restore their viscosities after application of the cosmetics. Also, for cosmetics, such as lip colors or lip glosses, for forming a cosmetic film on the skin or the like (hereinafter, referred to as makeup cosmetics), the state of finish is difficult to maintain. Hence, for the dextrin fatty acid esters serving as constituents of such cosmetics, new physical properties are desired for shortening the time required for the cosmetics to restore their viscosities.

Furthermore, if cosmetics have high properties of oozing oils (hereinafter, referred to as syneresis properties), their appearance is impaired. In addition, stability during preservation is reduced. Therefore, it is also desired that cosmetics also have low syneresis properties.

An objective of the present invention is to provide a dextrin fatty acid ester that offers a cosmetic having a restoring force and low syneresis properties, and a cosmetic containing the dextrin fatty acid ester.

Means for Solving the Problems

In accordance with one aspect of the present invention, a dextrin fatty acid ester is provided in which the dextrin has an average degree of glycopolymerization of 3 or more and 100 or less. The fatty acid includes one or more linear saturated fatty acids having 14 or more and 18 or less carbon atoms, and one or more branched saturated fatty acids having 14 or more and 18 or less carbon atoms. The molar fraction of the linear saturated fatty acid in the fatty acid is 0.75 or more and 0.95 or less. The average degree of substitution of the fatty acid per glucose unit is 1.5 or more and 2.0 or less.

In another aspect of the present invention, a cosmetic is provided that includes an oil and a dextrin fatty acid ester. The dextrin has an average degree of glycopolymerization of 3 or more and 100 or less. The fatty acid includes one or more linear saturated fatty acids having 14 or more and 18 or less carbon atoms and one or more branched saturated fatty acids having 14 or more and 18 or less carbon atoms. The molar fraction of the linear saturated fatty acid in the fatty acid is 0.75 or more and 0.95 or less. The average degree of substitution of the fatty acid per glucose unit is 1.5 or more and 2.0 or less.

The diligent studies of the inventor have revealed that among dextrin fatty acid esters that impart high thixotropy to cosmetics, a dextrin fatty acid ester comprising both of a linear saturated fatty acid and a branched saturated fatty acid wherein the numbers of carbon atoms thereof, the molar fractions of the linear saturated fatty acid and the branched saturated fatty acid, and the average degree of substitution fall within the ranges described above also has properties of imparting both of a restoring force and low syneresis properties to cosmetics. The restoring force refers to a force that largely increases a viscosity such that the viscosity is 50% or more with respect to the viscosity immediately before cancelation of a force applied to an oil containing a dextrin fatty acid ester, in a time as short as 20 seconds or shorter after the cancelation. Specifically, the dextrin in the dextrin fatty acid ester has an average degree of glycopolymerization of 3 or more and 100 or less, whereby the incapability of obtaining a soft gel is prevented while excessive reduction in the solubility of the dextrin fatty acid ester in an oil is prevented. The linear saturated fatty acid has 14 or more and 18 or less carbon atoms, whereby the restoring force imparted to cosmetics is enhanced. The branched saturated fatty acid has 14 or more and 18 or less carbon atoms, whereby the reaction efficiency between the dextrin and the fatty acid is improved while adequate viscosity properties are imparted to an oil. The molar fraction of the linear saturated fatty acid in the fatty acid is 0.75 or more and 0.95 or less, whereby a gelled oil has a smooth state while the restoring force is improved. The average degree of substitution of the fatty acid per glucose unit is 1.5 or more and 2.0 or less, whereby the syneresis properties are reduced.

According to one embodiment, the above-described dextrin fatty acid ester may be configured such that the average degree of glycopolymerization of the dextrin is 3 or more and 50 or less.

In this case, a soft gel is obtained while the solubility of the dextrin fatty acid ester in an oil is enhanced.

According to one embodiment, the above-described dextrin fatty acid ester may be configured such that the molar fraction of the linear saturated fatty acid in the fatty acid is 0.8 or more and 0.9 or less, and the average degree of substitution of the fatty acid per glucose unit is 1.65 or more and 1.80 or less.

In this case, the restoring force of an oil containing the dextrin fatty acid ester is improved while the syneresis properties are reduced.

According to one embodiment, the above-described dextrin fatty acid ester may be configured such that the linear saturated fatty acid is palmitic acid, and the branched saturated fatty acid is isopalmitic acid.

In this case, both of oil-gelling power and transparency are particularly excellent.

According to one embodiment, the above-described cosmetic may be configured such that the oil includes a volatile hydrocarbon oil.

In this case, the dextrin fatty acid ester, which has properties of imparting an excellent restoring force to cosmetics, imparts a restoring force to a volatile hydrocarbon oil having a low viscosity even if its content is small with respect to the volatile hydrocarbon oil. Therefore, the dextrin fatty acid ester particularly exerts effects in such a way that the degree of freedom of cosmetic formulation is enhanced.

BRIEF DESCRIPTION OF THE DRAWINGS

FIG. 1 is a table showing conditions for preparing dextrin fatty acid esters of Examples 1 to 6 and Comparative Examples 1 to 9.

FIG. 2 is a table showing the molar fractions of a linear saturated fatty acid and a branched saturated fatty acid, the average degree of substitution per glucose unit, and yields as to the dextrin fatty acid esters of Examples 1 to 6 and Comparative Examples 1 to 9.

FIG. 3 is a table showing a concentration and an initial viscosity as to samples of the dextrin fatty acid esters of Examples 1 to 6 and Comparative Examples 1 to 9 each dissolved in mineral oil or isododecane.

FIG. 5 is a table showing results of evaluating the samples of the dextrin fatty acid esters of Examples 1 to 6 and Comparative Examples 1 to 9 each dissolved in mineral oil or isododecane.

FIG. 6 is a table showing results of evaluating a mascara containing the dextrin fatty acid ester of each of Examples and Comparative Examples.

FIG. 7 is a table showing results of evaluating a body oil containing the dextrin fatty acid ester of each of Examples and Comparative Examples.

FIG. 8 is a table showing results of evaluating a cleansing gel containing the dextrin fatty acid ester of each of Examples and Comparative Examples.

FIG. 9 is a table showing results of evaluating a hair treatment gel containing the dextrin fatty acid ester of each of Examples and Comparative Examples.

FIG. 10 is a table showing results of evaluating a lip color containing the dextrin fatty acid ester of each of Examples and Comparative Examples.

FIG. 11 is a table showing results of evaluating a lip gloss containing the dextrin fatty acid ester of each of Examples and Comparative Examples.

FIG. 12 is a table showing results of evaluating an oil foundation containing the dextrin fatty acid ester of each of Examples and Comparative Examples.

FIG. 13 is a table showing results of evaluating a beauty oil containing the dextrin fatty acid ester of each of Examples and Comparative Examples.

FIG. 14 is a table showing results of evaluating a liquid rouge containing the dextrin fatty acid ester of each of Examples and Comparative Examples.

FIG. 15 is a table showing results of evaluating a gel eyeliner containing the dextrin fatty acid ester of each of Examples and Comparative Examples.

MODES FOR CARRYING OUT THE INVENTION

Figure 4:
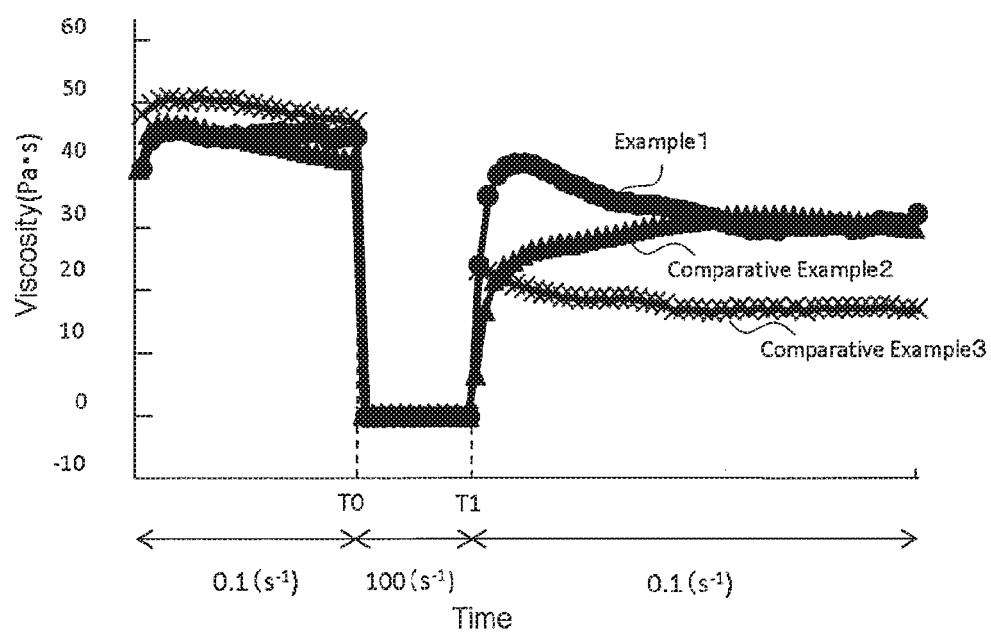
FIG. 4 is a graph illustrating the viscosities of the dextrin fatty acid esters in a still standing state and the viscosities of the dextrin fatty acid esters in a stirred state.

Hereinafter, the dextrin fatty acid ester and a cosmetic containing the dextrin fatty acid ester according to one embodiment will be described.

The dextrin fatty acid ester is an esterification product of a dextrin and a fatty acid and has a structure represented by the following chemical formula 1:

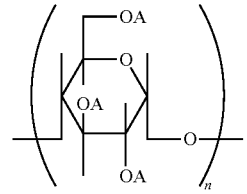

In the chemical formula 1, n represents the degree of polymerization of the dextrin, and A represents a fatty acid skeleton or hydrogen.

A decomposition product of a starch can be used as the dextrin of the dextrin fatty acid ester. The starch that can be used is prepared with wheat, potato, corn, rice, cassava, mung bean, or the like as a raw material. A conventional method can be used as a decomposition method. For example, one or more of acid treatment, alkali treatment, and enzymatic treatment can be used.

The dextrin fatty acid ester comprises at least a dextrin fatty acid ester given below.

The average degree of glycopolymerization of the dextrin is 3 or more and 100 or less, particularly preferably 10 or more and 50 or less. Provided that the average degree of glycopolymerization is 3 or more, the dextrin fatty acid ester becomes wax-like. Therefore, failure to obtain a soft gel is thereby prevented. Provided that the average degree of glycopolymerization is 100 or less, problems are inhibited, such as excessive reduction in the solubility of the dextrin fatty acid ester in an oil caused by a high dissolution temperature of the dextrin fatty acid ester in the oil.

The fatty acid of the dextrin fatty acid ester comprises one or more linear saturated fatty acids having 14 or more and 18 or less carbon atoms and one or more branched saturated fatty acids having 14 or more and 18 or less carbon atoms.

Specific examples of the linear saturated fatty acid having 14 or more and 18 or less carbon atoms include myristic acid (the number of carbon atoms: 14), pentadecanoic acid (the number of carbon atoms: 15), palmitic acid (the number of carbon atoms: 16), heptadecanoic acid (the number of carbon atoms: 17), and stearic acid (the number of carbon atoms: 18). Among these linear saturated fatty acids, palmitic acid is preferred. Provided that the linear saturated fatty acid has 14 or more carbon atoms, the oil-gelling power is strengthened. Provided that the linear saturated fatty acid has 18 or less carbon atoms, the white turbidity of a gelled oil is prevented so that the transparency of the oil is ensured. Among the linear saturated fatty acids having 14 or more and 18 or less carbon atoms, a linear saturated fatty acid having 16 carbon atoms is excellent in both oil-gelling power and transparency.

Specific examples of the branched saturated fatty acid having 14 or more and 18 or less carbon atoms include isomyristic acid (the number of carbon atoms: 14), isopentadecanoic acid (the number of carbon atoms: 15), isopalmitic acid (the number of carbon atoms: 16), isoheptadecanoic acid (the number of carbon atoms: 17), and isostearic acid (the number of carbon atoms: 18). Among these branched saturated fatty acids, isopalmitic acid is preferred. Provided that the branched saturated fatty acid has 14 or more carbon atoms, sufficient viscosity properties are imparted even to an oil having a low viscosity. Provided that the branched saturated fatty acid has 18 or less carbon atoms, the bulkiness of the branched saturated fatty acid with respect to the dextrin is suppressed so that the difficult bonding of the branched saturated fatty acid to the dextrin during esterification reaction is controlled. Even though the branched saturated fatty acid is bonded to the dextrin, reduction in reaction efficiency caused by the difficult bonding of the linear saturated fatty acid to the dextrin is prevented because the bulkiness of the branched saturated fatty acid is suppressed. Particularly, a branched saturated fatty acid having 14 or more and 16 or less carbon atoms has good reaction efficiency because its bulkiness is suppressed.

The isomyristic acid comprises one or more isomyristic acids. Examples thereof include, but are not limited to, 11-methyltridecanoic acid and 12-methyltridecanoic acid. The isopalmitic acid comprises one or more isopalmitic acids. Examples thereof include, but are not limited to, 14-methylpentadecanoic acid and 2-hexyldecanoic acid.

The isostearic acid comprises one or more isostearic acids. For example, 5,7,7-trimethyl-2-(1,3,3-trimethylbutyl)-octanoic acid is aldol-type isostearic acid and can be produced as follows: first, branched aldehydes having 9 carbon atoms are obtained through the oxo reaction of isobutylene dimers. Then, a branched unsaturated aldehyde having 18 carbon atoms is obtained through the aldol condensation between these branched aldehydes. The obtained branched unsaturated aldehyde can be hydrogenated and oxidized to obtain the isostearic acid.

As another isostearic acid, 2-heptylundecanoic acid can be produced by subjecting nonyl alcohol to Guerbet reaction, followed by oxidation.

Methyl-branched isostearic acid in which the branched chain is a methyl group is obtained, for example, as a by-product from the dimer production of oleic acid (e.g., J. Amer. Oil Chem. Soc., 51, 522 (1974)). Examples thereof include a commercially available product from Emery Oleochemicals (hereinafter, referred to as Emery type). A starting material for the starting material dimer acid for the Emery-type isostearic acid may include linoleic acid, linolenic acid, or the like, in addition to the oleic acid.

Among the fatty acid skeletons constituting the dextrin fatty acid ester, the linear fatty acid skeleton has a molar fraction of 0.75 or more and 0.95 or less, particularly preferably 0.80 or more and 0.90 or less. Specifically, the molar ratio between the linear saturated fatty acid and the branched saturated fatty acid of the dextrin fatty acid ester is within the range of 75:25 to 95:5, particularly preferably 80:20 to 90:10.

Since the molar fraction of the linear saturated fatty acid with respect to the whole fatty acid is 0.95 or less, the white turbidity of a gelled oil is prevented so that the transparency of the oil is ensured. Also, a gel is prevented from becoming rough and non-smooth due to a small proportion of the branched saturated fatty acid. Since the molar fraction of the linear saturated fatty acid with respect to the whole fatty acid is 0.75 or more, the oil-gelling power is also prevented from being too low due to an excessively high proportion of the branched saturated fatty acid. This also prevents the degree of reduction in viscosity by the application of a force from being small by adding the dextrin fatty acid ester at a high concentration to an oil in order to gel the oil, and prevents the restoring force from being lost. The restoring force refers to a force that largely increases a viscosity such that the viscosity is 50% or more with respect to a viscosity immediately before cancellation of a force applied to an oil containing a dextrin fatty acid ester, in a time as short as 20 seconds or shorter after the cancellation.

The average degree of substitution of the fatty acid per glucose unit of the dextrin fatty acid ester is 1.5 or more and 2.0 or less, particularly preferably 1.65 or more and 1.80 or less. Provided that the average degree of substitution is 1.5 or more, the oil-gelling power is prevented from being reduced. This also prevents the promotion of the syneresis properties of allowing an oil to float on the surface of a cosmetic film or an oil to separate during preservation, due to low solubility of the dextrin fatty acid ester in an oil. Provided that the average degree of substitution is 2.0 or less, excessive increase in the amount of the fatty acid bonded to the dextrin is prevented. Therefore, the heat resistance of a gel is obtained in such a way that the gel is kept even at, for example, approximately 50° C. In other words, a stable gel cannot be prepared if the average degree of substitution of the fatty acid is too large or too small.

A dextrin fatty acid ester having properties of imparting both of an excellent restoring force and low syneresis properties to cosmetics is obtained by adjusting, to the ranges described above, the average degree of glycopolymerization of the dextrin, the number of carbon atoms of the linear saturated fatty acid ester, the number of carbon atoms of the branched saturated fatty acid ester, the molar fractions of the linear saturated fatty acid ester and the branched saturated fatty acid ester, and the average degree of substitution.

Examples of the dextrin fatty acid ester include the following:
(myristic acid/12-methyltridecanoic acid) dextrin,
(myristic acid/2-hexyldecanoic acid) dextrin,
(myristic acid/Emery-type isostearic acid) dextrin,
(palmitic acid/2-hexyldecanoic acid) dextrin,
(palmitic acid/2-heptylundecanoic acid) dextrin,
(stearic acid/5,7,7-trimethyl-2-(1,3,3-trimethylbutyl)-octanoic acid) dextrin,
(palmitic acid/2-hexyldecanoic acid/Emery-type isostearic acid) dextrin, and
(myristic acid/palmitic acid/2-hexyldecanoic acid) dextrin.

Particularly, the dextrin fatty acid ester preferably contains palmitic acid as the linear saturated fatty acid bonded to the dextrin and preferably contains isopalmitic acid such as 2-hexyldecanoic acid as the branched saturated fatty acid ester.

A conventional production method can be used as a method for producing the dextrin fatty acid ester. For example, a fatty acid chloride can be added to the dextrin in the presence of a basic catalyst such as pyridine, triethylamine, or 3-methylpyridine to produce the dextrin fatty acid ester.

The oil to be combined with the dextrin fatty acid ester is not particularly limited as long as the oil can be used as a material for cosmetics and is capable of producing effects such as an excellent restoring force and low syneresis properties by the combination with the dextrin fatty acid ester. One type of oil may be used, or plural types of oils may be used as a mixture. These oils include an oil that has a high viscosity (e.g., polybutene and castor oil) or a solid state (e.g., higher fatty acids and waxes) in itself, which may be used, for example, in combination with a liquid oil or dextrin fatty acid ester.

Examples of hydrocarbon oils include liquid paraffin, squalane, isoparaffin, isododecane, isohexadecane, heavy liquid isoparaffin, polybutene, and Vaseline. Examples of ester oils include glyceryl tri-2-ethylhexanoate, glyceryl tri(caprylate/caprate), diglyceryl mono-, di-, tri-, tetra-isostearate, polyglyceryl isostearate, neopentyl glycol dioctanoate, neopentyl glycol dicaprate, 2-cetyl ethylhexanoate, isopropyl myristate, isopropyl palmitate, butyl stearate, 2-ethylhexyl palmitate, isononyl isononanoate, isotridecyl isononanoate, stearyl stearate, isostearyl myristate, octyldodecyl myristate, octyldodecyl oleate, diisostearyl malate, and cholesteryl 12-hydroxystearate. Examples of higher fatty acids include myristic acid, palmitic acid, stearic acid, oleic acid, behenic acid, isostearic acid, erucic acid, linoleic acid, and linolenic acid. Examples of higher alcohols include lauryl alcohol, myristyl alcohol, cetyl alcohol, stearyl alcohol, behenyl alcohol, 2-hexyldecanol, 2-octyldecanol, oleyl alcohol, and isostearyl alcohol. Examples of animal or plant oils include olive oil, camellia oil, soybean oil, cottonseed oil, sesame oil, safflower oil, wheat germ oil, coix seed oil, rice oil, jojoba oil, castor oil, flaxseed oil, corn oil, rapeseed oil, coconut oil, palm oil, squalene, liquid lanoline, mink oil, egg yolk oil, and wool oil. Examples of waxes include paraffin wax, microcrystalline wax, ceresin wax, beeswax, carnauba wax, candelilla wax, hydrogenated castor oil, and rosin. Examples of silicone oils include dimethylpolysiloxane, cyclic silicone, methylphenylpolysiloxane, and modified silicone.

The volatile hydrocarbon oil to be combined with the dextrin fatty acid ester means a hydrocarbon oil having a kinematic viscosity (37.8° C.) in the range of 0.5 mm$^2$/s or more and 15 mm$^2$/s or less. A linear or branched form can be used as the volatile hydrocarbon oil. Examples of such volatile hydrocarbon oils include isoparaffin-based hydrocarbon oils such as isodecane, isododecane, isohexadecane, and isoparaffin. Examples of commercial products thereof include Permethyl 99A, Permethyl 101A, and Permethyl 102A (manufactured by Presperse Corp.), Isopar A, Isopar C, Isopar D, Isopar E, Isopar G, Isopar H, Isopar K, Isopar L, and Isopar M (manufactured by Exxon Mobil Corp.), Shellsol 71 (manufactured by Shell Chemicals), Soltrol 100, Soltrol 130, and Soltrol 220 (manufactured by Chevron Phillips Chemical Company), Isozol 400 (manufactured by Nippon Petrochemicals Co., Ltd.), Parleam 4 (manufactured by NOF Corp.), IP Solvent 1016, IP Solvent 1620, and IP Solvent 2028 (manufactured by Idemitsu Petrochemical Co., Ltd.), and Isohexadecane and Tetraisobutane 90 (manufactured by Bayer AG).

The cosmetic containing this dextrin fatty acid ester can be supplemented, if necessary, with general components that may be added to cosmetics, without impairing the effects brought about by the addition of the dextrin fatty acid ester. Examples thereof include beauty components, surfactants, film forming agents, aqueous components, oil components, antiseptics, antioxidants, ultraviolet absorbers, ultraviolet scattering agents, fragrances, and powders. Examples of the beauty components include vitamins, anti-inflammatory agents, and crude drugs.

Examples of the surfactants include nonionic surfactants, anionic surfactants, cationic surfactants, and amphoteric surfactants.

Examples of the nonionic surfactants include glycerin fatty acid esters and alkylene glycol adducts thereof, polyglycerin fatty acid esters and alkylene glycol adducts thereof, propylene glycol fatty acid esters and alkylene glycol adducts thereof, sorbitan fatty acid esters and alkylene glycol adducts thereof, sorbitol fatty acid esters and alkylene glycol adducts thereof, polyalkylene glycol fatty acid esters, sucrose fatty acid esters, polyoxyalkylene alkyl ethers, glycerin alkyl ethers, polyoxyethylene alkyl phenyl ethers, polyoxyethylene hydrogenated castor oil, alkylene glycol adducts of lanoline, polyoxyalkylene alkyl-commodified silicone, and polyether-modified silicone.

Examples of the anionic surfactants include inorganic and organic salts of fatty acids such as stearic acid and lauric acid, alkylbenzenesulfonates, alkylsulfonates, α-olefinsulfonates, dialkyl sulfosuccinates, α-sulfonated fatty acid salts, acyl methyl taurine salts, N-methyl-N-alkyl taurine salts, polyoxyethylene alkyl ether sulfates, polyoxyethylene alkyl phenyl ether sulfates, alkyl phosphates, polyoxyethylene alkyl ether phosphates, polyoxyethylene alkyl phenyl ether phosphates, N-acylamino acid salts, N-acyl-N-alkylamino acid salts, o-alkyl-substituted malate, and alkyl sulfosuccinates.

Examples of the cationic surfactants include alkylamine salts, polyamine and alkanolamine fatty acid derivatives, alkyl quaternary ammonium salts, and cyclic quaternary ammonium salts.

The amphoteric surfactants include amino acid-type or betaine-type carboxylic acids, sulfuric acid esters, sulfonic acids, and phosphoric acid esters. An amphoteric surfactant safe to human bodies can be used. Examples thereof include N,N-dimethyl-N-alkyl-N-carboxylmethyl ammonium betaine, N,N-dialkylaminoalkylene carboxylic acid, N,N,N-trialkyl-N-sulfoalkylene ammonium betaine, N,N-dialkyl-N,N-bis(polyoxyethylene sulfuric acid) ammonium betaine, 2-alkyl-1-hydroxyethyl-1-carboxymethyl imidazolinium betaine, and lecithin.

Examples of the film forming agents include: polymer emulsions such as alkyl acrylate copolymer emulsions, alkyl acrylate-styrene copolymer emulsions, polyvinyl acetate emulsions, and vinylpyrrolidone-styrene copolymer emulsions; silicone-based resins such as trimethylsiloxysilicic acid, trimethylsiloxysilylpropylcarbamic acid, fluorine-modified silicone, and acrylic silicone; latexes such as polyvinyl alcohol, polyvinyl acetate, and polyalkyl acetate; and cellulose derivatives such as dextrin, alkylcellulose, and nitrocellulose.

Examples of the aqueous components include: lower alcohols such as ethyl alcohol and butyl alcohol; glycols such as propylene glycol, 1,3-butylene glycol, 1,2-pentanediol, dipropylene glycol, and polyethylene glycol; glycerols such as glycerin, diglycerin, and polyglycerin; and extracts of plants such as aloe vera, witch-hazel, hamamelis, cucumber, lemon, lavender, and rose. Examples of water-soluble polymers include: natural products such as guar gum, sodium chondroitin sulfate, sodium hyaluronate, gum arabic, sodium alginate, and carrageenan; semisynthetic products such as methylcellulose, hydroxyethylcellulose, and carboxymethylcellulose; and synthetic products such as carboxyvinyl polymers, alkyl-added carboxyvinyl polymers, and sodium polyacrylate. Examples include proteins, mucopolysaccharides, collagen, elastin, and keratin.

Examples of the oil components include dextrin fatty acid esters other than the dextrin fatty acid ester described above. Examples thereof include dextrin palmitate, dextrin myristate, dextrin (palmitate/ethylhexanoate), and dextrin isostearate. Other examples of the oil components include inulin fatty acid esters such as inulin stearate.

Examples of the antiseptics include p-hydroxybenzoate ester, phenoxyethanol, and 1,2-pentanediol.

Examples of the antioxidants include α-tocopherol and ascorbic acid.

Examples of the ultraviolet absorbers include benzophenone-based, PABA-based, cinnamic acid-based, and salicylic acid-based ultraviolet absorbers, 4-tert-butyl-4'-methoxydibenzoylmethane, and oxybenzone.

Examples of the powders include titanium oxide, zinc oxide, iron oxide yellow, iron oxide black, iron red, carbon black, mica, sericite, talc, kaolin, barium sulfate, bentonite, smectite, boron nitride, iron blue, ultramarine blue, bismuth oxychloride, titanium dioxide, aluminum powders, magnesium stearate, zinc stearate, N-acyl lysine, nylon, organic pigments, organic dyes, nylon powders, urethane powders, and spherical silicone resin powders.

Also, these powders can each be treated with a fluorine compound, silicone oil, metallic soap, a surfactant, a dextrin fatty acid ester, an inulin fatty acid ester, a fat, or the like and used.

One or more of these dextrin fatty acid esters are contained in a cosmetic containing an oil as a base. The content of the dextrin fatty acid ester in the cosmetic is preferably 1% by weight or more and 20% by weight or less. Provided that the content is 1% by weight or more, a gel having a restoring force is prepared. Provided that the content is 20% by weight or less, a gel is softened and becomes a sol state, which is a flowable state, from the gel by the application of a force. When the oil for dissolving the dextrin fatty acid ester is a volatile hydrocarbon oil, the content of the volatile hydrocarbon oil is preferably larger than that of other oils such as mineral oil, for example, 3% by weight or more and 20% by weight or less, for preparing a gel having a restoring force, because the volatile hydrocarbon oil has a low viscosity.

The cosmetic containing the dextrin fatty acid ester mentioned above has both of an excellent restoring force and low syneresis properties. This cosmetic is in a gel state without a force. The gel is disrupted by the application of a force so that the gel becomes a sol state which is a thick liquid state. The cosmetic further returns to the gel state when left.

Although conventional dextrin fatty acid esters impart high thixotropy to cosmetics, an oil supplemented with the dextrin fatty acid ester described above produces a restoring force, which cannot be obtained in oils supplemented with the conventional dextrin fatty acid esters. Therefore, when the dextrin fatty acid ester is used in a cosmetic, the amount of the dextrin fatty acid ester added to obtain a viscosity practical as cosmetics will be smaller than conventional ones.

Owing to the restoring force by the dextrin fatty acid ester, the viscosity of the cosmetic is reduced by the application of a force, for example, in order to take out the cosmetic from a preservation container containing the cosmetic. Therefore, the cosmetic, even if highly viscous, is easily taken out of the preservation container. Also, the taken out cosmetic resists flowing down when taken up on the palm or put on the face or the body. For a cosmetic of type in which the cosmetic is used by shaking the preservation container and thereby dispersing a dispersoid in a dispersion medium, the viscosity is reduced during stirring whereas the viscosity is restored in a short time after the completion of stirring. Therefore, the cosmetic with the dispersoid uniformly dispersed can be taken out of the preservation container. Furthermore, preservation stability is improved because syneresis is suppressed during preservation.

Conventional dextrin fatty acid esters that impart high thixotropy to cosmetics have a low thickening effect on volatile and low viscous oils, such as isododecane, which are often used in makeup cosmetics, and thus need to be added in large amounts. Hence, cosmetics containing the conventional dextrin fatty acid esters hardly reduce their viscosities by the application of a force due to the large amounts of the dextrin fatty acid esters added. By contrast, the dextrin fatty acid ester having properties of imparting both of an excellent restoring force and low syneresis properties as mentioned above produces a restoring force even at a low content and therefore increases the degree of freedom of cosmetic formulation.

Since the viscosity of the cosmetic is reduced by the application of a force, the cosmetic spreads well and is easy to apply. Therefore, cosmetics, such as mascaras, lip colors, lip glosses, oil foundations, liquid rouges, eyeliners, or manicures, for forming a cosmetic film on eyelashes, the skin, fingernails, etc. attain a beautiful finish because the cosmetics are easily applied uniformly with a desired thickness. At the completion of application of the cosmetics, the cosmetics restore their viscosities. Therefore, the cosmetics are prevented from flowing down or being smudged and thus easily maintain the cosmetic film state of completion of application. The cosmetic film thus formed restores a viscosity if the viscosity is reduced by the movement of lips, regions around eyes, etc. having the formed cosmetic film. Thus, the cosmetic film is prevented, for example, from coming off or being deteriorated and lasts long (long lasting look). Thus, the cosmetic film state of a finish is maintained over time owing to the excellent restoring force and low syneresis properties by the dextrin fatty acid ester.

Each effect mentioned above is obtained because the dextrin fatty acid ester is a gelling agent that confers a restoring force.

A cosmetic containing the dextrin fatty acid ester possesses a viscosity practical as cosmetics. The cosmetic also has high transparency and is also excellent in high-temperature stability which allows the shape to be retained even at a high temperature, for example, 50° C., solubility in a plurality of oils, etc. Therefore, the dextrin fatty acid ester can be used in diverse cosmetics. The practical use of dextrin fatty acid esters for diverse cosmetics may also be improved by the recipe adjustment of each component constituting the cosmetics. However, such recipe adjustment ultimately takes a lot of trial and error on the selection or recipe of other components for each cosmetic. The configuration of the dextrin fatty acid ester mentioned above reduces such inconvenience in each cosmetic by virtue of the characteristics of the dextrin fatty acid ester.

EXAMPLES

Hereinafter, Examples and Comparative Examples will be described with reference to FIGS. 1 to 15. However, the present invention is not intended to be limited by Examples below.

The table of FIG. 1 shows the conditions for preparing the dextrin fatty acid esters of Examples 1 to 6 and Comparative Examples 1 to 9.

The table of FIG. 2 shows the molar fractions, average degree of substitution, and yields as to the synthesized products of Examples 1 to 6 and Comparative Examples 1 to 9. The molar fractions are shown in calculated percentage in the table. The analysis equipment used in these Examples was as described below.

Average Degree of Substitution

The average degree of substitution was determined by the measurement of the amount of an alkali required for alkali decomposition, i.e., saponification value measurement.
Molar fraction of fatty acid in synthesized product The molar fraction was determined by the GC measurement of the fatty acid after alkali decomposition.

GC Analysis

GC equipment: gas chromatograph GC-2010 manufactured by Shimadzu Corp.

Column: InertCap FFAP manufactured by GL Sciences Inc.

Detector: FID

Measurement of degree of restoration

Viscoelasticity measurement apparatus: MCR100 manufactured by Paar Physica

Measurement jig: CP25-2

Example 1

An amount of 73 g of a dextrin having an average degree of polymerization of 20 was dispersed at 80° C. in 219 g of dimethylformamide as a solvent and 99 g of pyridine as a basic catalyst. To the dispersion, 223 g of palmitic acid chloride as a linear saturated fatty acid chloride and 52 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 81% and 19%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 220 g of a white powder. The recovered dextrin fatty acid ester was subjected to saponification value measurement and GC analysis after alkali decomposition to determine that the average degree of substitution of the fatty acid was 1.67, the molar fraction of the linear saturated fatty acid bonded to the dextrin in the fatty acid was 85%, and the molar fraction of the branched saturated fatty acid bonded to the dextrin in the fatty acid was 15%.

Example 2

An amount of 72 g of a dextrin having an average degree of polymerization of 3 was dispersed at 80° C. in 72 g of heptane as a solvent and 116 g of β-picoline as a basic catalyst. To the dispersion, 207 g of myristic acid chloride as a linear saturated fatty acid chloride and 48 g of Emery-type isostearic acid chloride as a branched saturated fatty acid chloride were added dropwise in 60 minutes. The molar fractions of the linear saturated fatty acid and the branched saturated fatty acid added dropwise were 84% and 16%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 205 g of a white powder. The recovered dextrin fatty acid ester was subjected to saponification value measurement and GC analysis after alkali decomposition to determine that the average degree of substitution of the fatty acid was 1.73, the molar fraction of the linear saturated fatty acid bonded to the dextrin was 88%, and the molar fraction of the branched saturated fatty acid bonded to the dextrin was 12%.

Example 3

An amount of 68 g of a dextrin having an average degree of polymerization of 50 was dispersed at 80° C. in 135 g of N-methylpyrrolidone as a solvent and 116 g of β-picoline as a basic catalyst. To the dispersion, 206 g of stearic acid chloride as a linear saturated fatty acid chloride and 79 g of isomyristic acid chloride (12-methyltridecanoic acid chloride) as a branched saturated fatty acid chloride were added dropwise in 60 minutes. The molar fractions of the linear saturated fatty acid and the branched saturated fatty acid added dropwise were 68% and 32%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 251 g of a white powder. The recovered dextrin fatty acid ester was subjected to saponification value measurement and GC analysis after alkali decomposition to determine that the average degree of substitution of the fatty acid was 1.99, the molar fraction of the linear saturated fatty acid bonded to the dextrin was 75%, and the molar fraction of the branched saturated fatty acid bonded to the dextrin was 25%.

Example 4

An amount of 77 g of a dextrin having an average degree of polymerization of 20 was dispersed at 80° C. in 193 g of dimethylformamide as a solvent and 116 g of β-picoline as a basic catalyst. To the dispersion, 253 g of palmitic acid chloride as a linear saturated fatty acid chloride and 24 g of Emery-type isostearic acid chloride as a branched saturated fatty acid chloride were added dropwise in 60 minutes. The molar fractions of the linear saturated fatty acid and the branched saturated fatty acid added dropwise were 92% and 8%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 203 g of a white powder. The recovered dextrin fatty acid ester was subjected to saponification value measurement and GC analysis after alkali decomposition to determine that the average degree of substitution of the fatty acid was 1.52, the molar fraction of the linear saturated fatty acid bonded to the dextrin was 95%, and the molar fraction of the branched saturated fatty acid bonded to the dextrin was 5%.

Example 5

An amount of 70 g of a dextrin having an average degree of polymerization of 20 was dispersed at 80° C. in 211 g of dimethylformamide as a solvent and 116 g of β-picoline as a basic catalyst. To the dispersion, 93 g of myristic acid chloride as a linear saturated fatty acid chloride, 103 g of palmitic acid chloride as a linear saturated fatty acid chloride, and 69 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 75% and 25%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 192 g of a white powder. The recovered dextrin fatty acid ester was subjected to saponification value measurement and GC analysis after alkali decomposition to determine that the average degree of substitution of the fatty acid was 1.80, the molar fraction of the linear saturated fatty acid bonded to the dextrin was 80%, and the molar fraction of the branched saturated fatty acid bonded to the dextrin was 20%.

Example 6

An amount of 74 g of a dextrin having an average degree of polymerization of 10 was dispersed at 80° C. in 221 g of dimethylformamide as a solvent and 116 g of β-picoline as a basic catalyst. To the dispersion, 237 g of palmitic acid chloride as a linear saturated fatty acid chloride and 39 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 86% and 14%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 211 g of a white powder. The recovered dextrin fatty acid ester was subjected to saponification value measurement and GC analysis after alkali decomposition to determine that the average degree of substitution of the fatty acid was 1.61, the molar fraction of the linear saturated fatty acid bonded to the dextrin was 90%, and the molar fraction of the branched saturated fatty acid bonded to the dextrin was 10%.

Comparative Example 1

An amount of 74 g of a dextrin having an average degree of polymerization of 2 was dispersed at 80° C. in 221 g of dimethylformamide as a solvent and 116 g of β-picoline as a basic catalyst. To the dispersion, 220 g of palmitic acid chloride as a linear saturated fatty acid chloride and 55 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 80% and 20%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 230 g of a white powder. The recovered dextrin fatty acid ester was subjected to saponification value measurement and GC analysis after alkali decomposition to determine that the average degree of substitution of the fatty acid was 1.80, the molar fraction of the linear saturated fatty acid bonded to the dextrin was 83%, and the molar fraction of the branched saturated fatty acid bonded to the dextrin was 17%.

Comparative Example 2

An amount of 77 g of a dextrin having an average degree of polymerization of 20 was dispersed at 80° C. in 232 g of dimethylformamide as a solvent and 116 g of β-picoline as a basic catalyst. To the dispersion, 275 g of palmitic acid chloride as a linear saturated fatty acid chloride was added dropwise in 60 minutes. Specifically, the molar fractions of the linear saturated fatty acid and the branched saturated fatty acid added dropwise were 100% and 0%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 205 g of a white powder. The recovered dextrin fatty acid ester was subjected to saponification value measurement and GC analysis after alkali decomposition to determine that the average degree of substitution of the fatty acid was 1.50, and the molar fraction of the linear saturated fatty acid bonded to the dextrin was 100%.

Comparative Example 3

An amount of 77 g of a dextrin having an average degree of polymerization of 20 was dispersed at 80° C. in 232 g of dimethylformamide as a solvent and 116 g of β-picoline as a basic catalyst. To the dispersion, 206 g of palmitic acid chloride as a linear saturated fatty acid chloride and 41 g of 2-ethylhexanoic acid chloride having 8 carbon atoms as a branched saturated fatty acid chloride were added dropwise in 60 minutes. The molar fractions of the linear saturated fatty acid and the branched saturated fatty acid added dropwise were 75% and 25%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 185 g of a white powder. The recovered dextrin fatty acid ester was subjected to saponification value measurement and GC analysis after alkali decomposition to determine that the average degree of substitution of the fatty acid was 1.50, the molar fraction of the linear saturated fatty acid bonded to the dextrin was 87%, and the molar fraction of the branched saturated fatty acid bonded to the dextrin was 13%.

Comparative Example 4

An amount of 56 g of a dextrin having an average degree of polymerization of 20 was dispersed at 80° C. in 168 g of dimethylformamide as a solvent and 116 g of β-picoline as a basic catalyst. To the dispersion, 217 g of palmitic acid chloride as a linear saturated fatty acid chloride and 58 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 79% and 21%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 201 g of a white powder. The recovered dextrin fatty acid ester was subjected to saponification value measurement and GC analysis after alkali decomposition to determine that the average degree of substitution of the fatty acid was 2.06, the molar fraction of the linear saturated fatty acid bonded to the dextrin was 83%, and the molar fraction of the branched saturated fatty acid bonded to the dextrin was 17%.

Comparative Example 5

An amount of 81 g of a dextrin having an average degree of polymerization of 20 was dispersed at 80° C. in 243 g of dimethylformamide as a solvent and 116 g of β-picoline as a basic catalyst. To the dispersion, 231 g of palmitic acid chloride as a linear saturated fatty acid chloride and 44 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 84% and 16%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 189 g of a white powder. The recovered dextrin fatty acid ester was subjected to saponification value measurement and GC analysis after alkali decomposition to determine that the average degree of substitution of the fatty acid was 1.43, the molar fraction of the linear saturated fatty acid bonded to the dextrin was 87%, and the molar fraction of the branched saturated fatty acid bonded to the dextrin was 13%.

Comparative Example 6

An amount of 72 g of a dextrin having an average degree of polymerization of 20 was dispersed at 80° C. in 216 g of dimethylformamide as a solvent and 116 g of β-picoline as a basic catalyst. To the dispersion, 184 g of lauric acid having 12 carbon atoms as a linear saturated fatty acid chloride and 44 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 84% and 16%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 169 g of a white powder. The recovered dextrin fatty acid ester was subjected to saponification value measurement and GC analysis after alkali decomposition to determine that the average degree of substitution of the fatty acid was 1.62, the molar fraction of the linear saturated fatty acid bonded to the dextrin was 88%, and the molar fraction of the branched saturated fatty acid bonded to the dextrin was 12%.

Comparative Example 7

An amount of 52 g of a dextrin having an average degree of polymerization of 20 was dispersed at 80° C. in 157 g of dimethylformamide as a solvent and 116 g of β-picoline as a basic catalyst. To the dispersion, 275 g of palmitic acid as a linear saturated fatty acid chloride was added dropwise in 60 minutes. Specifically, the molar fractions of the linear saturated fatty acid and the branched saturated fatty acid added dropwise were 100% and 0%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 190 g of a white powder. The recovered dextrin fatty acid ester was subjected to saponification value measurement and GC analysis after alkali decomposition to determine that the average degree of substitution of the fatty acid was 2.20, and the molar fraction of the linear saturated fatty acid bonded to the dextrin was 100%.

Comparative Example 8

An amount of 60 g of a dextrin having an average degree of polymerization of 20 was dispersed at 80° C. in 180 g of dimethylformamide as a solvent and 116 g of β-picoline as a basic catalyst. To the dispersion, 165 g of palmitic acid as a linear saturated fatty acid chloride and 110 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 60% and 40%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 172 g of a white powder. The recovered dextrin fatty acid ester was subjected to saponification value measurement and GC analysis after alkali decomposition to determine that the average degree of substitution of the fatty acid was 1.90, the molar fraction of the linear saturated fatty acid bonded to the dextrin was 63%, and the molar fraction of the branched saturated fatty acid bonded to the dextrin was 37%.

Comparative Example 9

An amount of 66 g of a dextrin having an average degree of polymerization of 20 was dispersed at 80° C. in 199 g of dimethylformamide as a solvent and 116 g of β-picoline as a basic catalyst. To the dispersion, 161 g of myristic acid chloride as a linear saturated fatty acid chloride and 96 g of isopalmitic acid chloride as a branched saturated fatty acid chloride were added dropwise in 60 minutes. The isopalmitic acid chloride was 2-hexyldecanoic acid chloride. The molar fractions of the linear saturated fatty acid and the branched saturated fatty acid added dropwise were 65% and 35%, respectively, in terms of percentage. After the completion of dropwise addition, the mixture was reacted at a reaction temperature of 95° C. for 4 hours. The reaction solution was precipitated in methanol and then filtered. Solid matter was washed with methanol and dried to obtain 171 g of a white powder. The recovered dextrin fatty acid ester was subjected to saponification value measurement and GC analysis after alkali decomposition to determine that the average degree of substitution of the fatty acid was 1.70, the molar fraction of the linear saturated fatty acid bonded to the dextrin was 70%, and the molar fraction of the branched saturated fatty acid bonded to the dextrin was 30%.

[Evaluation]

Next, Examples 1 to 6 and Comparative Examples 1 to 9 were evaluated.

First, a measurement sample containing a general oil as a base and a measurement sample containing a volatile hydrocarbon oil as a base were prepared using each of the dextrin fatty acid esters of Examples 1 to 6 and the dextrin fatty acid esters of Comparative Examples 1 to 9. The volatile hydrocarbon oil volatilizes after application of cosmetics and is used in, for example, oil foundations, mascaras, and eyeliners.

The general oil used was mineral oil. Each of the dextrin fatty acid esters of Examples 1 to 6 and the dextrin fatty acid esters of Comparative Examples 1 to 9 was added to mineral oil of 90° C. and dissolved therein by heating. A 30-ml vial (manufactured by Nichiden Rika Glass Co., Ltd.) was filled with 20 g of the solution and left at room temperature for 10 days for gelling. After a lapse of 10 days, the gel was disrupted by stirring to obtain six measurement samples respectively containing the dextrin fatty acid esters of Examples 1 to 6 and nine measurement samples respectively containing the dextrin fatty acid esters of Comparative Examples 1 to 9.

The volatile hydrocarbon oil used was isododecane. Each of the dextrin fatty acid esters of Examples 1 to 6 and the dextrin fatty acid esters of Comparative Examples 1 to 9 was added to isododecane of 70° C. and dissolved therein by heating. A 30-ml vial (manufactured by Nichiden Rika Glass Co., Ltd.) was filled with 20 g of the solution and left at room temperature for 10 days. After a lapse of 10 days, the gel was disrupted by stirring to obtain six measurement samples respectively containing the dextrin fatty acid esters of Examples 1 to 6 and nine measurement samples respectively containing the dextrin fatty acid esters of Comparative Examples 1 to 9.

The table of FIG. 3 shows the dissolution concentrations of the dextrin fatty acid esters of Examples 1 to 6 and the dextrin fatty acid esters of Comparative Examples 1 to 9, and the viscosities of the measurement samples.

Degree of Restoration

Next, the degree of restoration was measured for each measurement sample containing mineral oil as a base and each measurement sample containing isododecane as a base. The restoring force is the amount of the viscosity increased per unit time of the measurement sample form when a force was applied to each gelled measurement sample to when the force was canceled.

At a measurement temperature of 25° C., the viscosity (Pa·s) was measured while the sample was rotated at a rotational speed of 0.1 ($s^{-1}$) for 4 minutes, 100 ($s^{-1}$) for 2 minutes, and 0.1 ($s^{-1}$) for 8 minutes using a measurement jig. The rotational speed of 0.1 ($s^{-1}$) corresponds to a still standing state, and the rotational speed of 100 ($s^{-1}$) corresponds to a stirred state.

FIG. 4 shows a graph illustrating thixotropy as to the measurement sample containing the dextrin fatty acid ester of Example 1 and the measurement samples containing the dextrin fatty acid esters of Comparative Examples 2 and 3. The ordinate shows viscosity (Pa·s), and the abscissa shows time. In the measurement sample of Example 1, the viscosity was reduced to almost 0 Pa·s from the rotational speeds 0.1 ($s^{-1}$) to 100 ($s^{-1}$), and the viscosity was temporarily brought back to near the original viscosity from the rotational speeds 100 ($s^{-1}$) to 0.1 ($s^{-1}$). On the other hand, although the viscosities of the measurement samples of Comparative Examples 2 and 3 were increased from the rotational speeds 100 ($s^{-1}$) to 0.1 ($s^{-1}$), the amount of change in the viscosities was remarkably small, as compared with Example 1.

When the viscosity immediately before the rotational speed reached 100 ($s^{-1}$) from 0.1 ($s^{-1}$) (start time T0) was defined as an initial viscosity, the time to restoration (time required from when the rotational speed reached 0.1 ($s^{-1}$) from 100 ($s^{-1}$) (finish time T1) to when the viscosity reached half of the initial viscosity) was measured.

A time to restoration within 10 seconds was indicated by a double circle, a time to restoration of more than 10 seconds and within 20 seconds was indicated by a circle, and a time to restoration of more than 20 seconds or a viscosity that failed to reach half of the initial viscosity was indicated by an x-mark. Specifically, a measurement sample rated as a double circle or a circle has a restoring force.

As shown in the table of FIG. 5, among the measurement samples of Examples 1 to 6 containing mineral oil as a base, the measurement sample of Example 4 had a time to restoration of more than 10 seconds and within 20 seconds, and the viscosities of the other samples reached half of the initial viscosity within 10 seconds. The viscosity of the measurement sample of Comparative Example 7 reached half of the initial viscosity within 10 seconds, and the viscosities of the measurement samples of Comparative Examples 1, 2, 4, and 6 reached half of the initial viscosity in a time of more than 10 seconds and within 20 seconds. The viscosities of the measurement samples of Comparative Examples 3, 5, 8, and 9 failed to reach half of the initial viscosity within 20 seconds. The measurement sample of Comparative Example 9 neither obtained a sufficient viscosity nor was gelled.

Among the measurement samples of Examples 1 to 6 containing isododecane as a base, the measurement sample of Example 3 had a time to restoration of more than 10 seconds and within 20 seconds, and the viscosities of the other samples reached half of the initial viscosity within 10 seconds. The viscosity of the measurement sample of Comparative Example 7 reached half of the initial viscosity within 10 seconds. The viscosities of the measurement samples of Comparative Examples 1, 4, and 6 reached half of the initial viscosity in a time of more than 10 seconds and within 20 seconds. The viscosities of the measurement samples of Comparative Examples 2, 3, 5, 8, and 9 failed to reach half of the initial viscosity within 20 seconds.

Syneresis Properties

For each of the measurement samples of Examples 1 to 6 and the measurement samples of Comparative Examples 1 to 9 containing mineral oil as a base and the measurement samples of Examples 1 to 6 and the measurement samples of Comparative Examples 1 to 9 containing isododecane as a base, the gel was disrupted by stirring and left standing at a temperature of 25° C., and the presence or absence of syneresis was determined. A state where syneresis was not observed even after a lapse of 1 week was indicated by a double circle, a state where syneresis was observed slightly, but hardly, after 1 week was indicated by a circle, and a state where syneresis was observed after a lapse of 1 day was indicated by an x-mark.

Syneresis was observed in none of the measurement samples of Examples 1, 5, and 6 containing mineral oil as a base, and syneresis was hardly observed in the measurement samples of Examples 2 to 4. Syneresis was observed in neither of the measurement samples of Comparative Examples 8 and 9 containing mineral oil as a base, and syneresis was hardly observed in the measurement sample of Comparative Example 3. Syneresis was observed after a lapse of 1 day in the remaining measurement samples of Comparative Examples 1, 2, and 4 to 7.

Syneresis was observed in none of the measurement samples of Examples 1 and 4 to 6 containing isododecane as a base, and syneresis was hardly observed in the measurement samples of Examples 2 to 4. Syneresis was observed in neither of the measurement samples of Comparative Examples 8 and 9 containing isododecane as a base, and syneresis was hardly observed in the measurement sample of Comparative Example 3. Syneresis was observed after a lapse of 1 day in the remaining measurement samples of Comparative Examples 1, 2, and 4 to 7.

Thus, all of the measurement samples of Examples 1 to 6 were rated as a double circle or a circle for the degree of restoration and as a double circle or a circle for the low syneresis properties in both of the solvents mineral oil and isododecane, and thus had both of an excellent restoring force and low syneresis properties. On the other hand, all of the measurement samples of Comparative Examples 1 to 9 were rated as an x-mark for one or both of the degree of restoration and the syneresis properties in mineral oil as a solvent and were inferior. Also, all of the measurement samples of Comparative Examples 1 to 9 were rated as an x-mark for one or both of the degree of restoration and the syneresis properties in isododecane as a solvent and were inferior.

Viscosity

For each of the measurement samples of Examples 1 to 6 and the measurement samples of Comparative Examples 1 to 9 containing mineral oil as a base and the measurement samples of Examples 1 to 6 and the measurement samples of Comparative Examples 1 to 9 containing isododecane as a base, the viscosity upon disruption of the gel was measured using a viscoelasticity measurement apparatus. A level at which the gel became a flowable liquid when disrupted by stirring was indicated by a double circle, a level at which the gel became a thick liquid when disrupted was indicated by a circle, and a level at which the gel was hardly flowable when disrupted was indicated by an x-mark.

All of the measurement samples of Examples 1 to 6 containing mineral oil as a base were rated as a double circle or a circle for the viscosity when the gel was disrupted. On the other hand, the measurement samples of Comparative Examples 2, 4, 6, and 7 were rated as a circle for the viscosity when the gel was disrupted, whereas the remaining measurement samples of Comparative Examples 1, 3, 5, 8, and 9 were rated as an x-mark for the viscosity when the gel was disrupted.

All of the measurement samples of Examples 1 to 6 containing isododecane as a base were rated as a double circle or a circle for the viscosity when the gel was disrupted. On the other hand, the measurement sample of Comparative Example 7 was rated as a double circle for the viscosity when the gel was disrupted, and the measurement samples of Comparative Examples 2, 4, and 6 were rated as a circle for the viscosity when the gel was disrupted, whereas the remaining measurement samples of Comparative Examples 1, 3, 5, 8, and 9 were rated as an x-mark for the viscosity when the gel was disrupted.

Transparency

For each of the measurement samples of Examples 1 to 6 and the measurement samples of Comparative Examples 1 to 9 containing mineral oil as a base and the measurement samples of Examples 1 to 6 and the measurement samples of Comparative Examples 1 to 9 containing isododecane as a base, transparency was visually checked. A state where turbidity was not visually observed was indicated by a double circle, a state where turbidity was slightly present was indicated by a circle, and a state where turbidity was determined to be present was indicated by an x-mark.

Turbidity was observed in none of the measurement samples of Examples 1 to 6 containing mineral oil as a base. Turbidity was observed in none of the measurement samples of Comparative Examples 3, 6, 8, and 9. Turbidity was slightly present in the measurement sample of Comparative Example 1, and turbidity was observed in the measurement samples of Comparative Examples 2, 4, 5, and 7.

Turbidity was observed in none of the measurement samples of Examples 1 to 6 containing isododecane as a base. Turbidity was observed in none of the measurement samples of Comparative Examples 3, 6, 8, and 9. Turbidity was slightly present in the measurement sample of Comparative Example 1, and turbidity was observed in the measurement samples of Comparative Examples 2, 4, 5, and 7.

Dissolution Temperature

The dextrin fatty acid esters of Examples 1 to 6 and the dextrin fatty acid esters of Comparative Examples 1 to 9 were evaluated for their dissolution temperatures in mineral oil. Also, the dextrin fatty acid esters of Examples 1 to 6 and the dextrin fatty acid esters of Comparative Examples 1 to 9 were evaluated for their dissolution temperatures in isododecane.

In the case of dissolving each dextrin fatty acid ester in mineral oil, a level at which the dextrin fatty acid ester was dissolved in mineral oil of 90° C. was indicated by a double circle, a level at which the dextrin fatty acid ester was dissolved in mineral oil of 100° C. was indicated by a circle, and a level at which the dextrin fatty acid ester was dissolved in mineral oil with a temperature higher than 100° C. was indicated by an x-mark.

In the case of dissolving each dextrin fatty acid ester in isododecane, a level at which the dextrin fatty acid ester was dissolved in isododecane of 75° C. was indicated by a double circle, a level at which the dextrin fatty acid ester was dissolved in isododecane of 85° C. was indicated by a circle, and a level at which the dextrin fatty acid ester was dissolved in isododecane with a temperature higher than 85° C. was indicated by an x-mark.

The dextrin fatty acid esters of Examples 1, 2, 5, and 6 were dissolved in mineral oil of 90° C., and the dextrin fatty acid esters of Examples 3 and 4 were dissolved in mineral oil of 100° C. The dextrin fatty acid esters of Comparative Examples 1 and 7 to 9 were dissolved in mineral oil of 90° C., and the dextrin fatty acid esters of Comparative Examples 2, 3, 5, and 6 were dissolved in mineral oil of 100° C. The dextrin fatty acid ester of Comparative Example 4 was dissolved in mineral oil with a temperature higher than 100° C.

The dextrin fatty acid esters of Examples 1, 2, 5, and 6 were dissolved in isododecane of 75° C., and the dextrin fatty acid esters of Examples 3 and 4 were dissolved in isododecane of 85° C. The dextrin fatty acid esters of Comparative Examples 1, 3, 8, and 9 were dissolved in isododecane of 75° C., and isododecane of Comparative Examples 2 and 5 to 7 were dissolved in isododecane of 85° C. The dextrin fatty acid ester of Comparative Example 4 was dissolved in isododecane with a temperature higher than 85° C.

Hereinafter, Examples of cosmetics produced using the dextrin fatty acid esters of Examples will be described with reference to FIGS. 6 to 15. In FIGS. 6 to 15, the proportion of each component is indicated by % by weight.

Example A

Cosmetic: mascara
Components
(1) Dextrin fatty acid ester (2) Isododecane (Permethyl 99A manufactured by Presperse Corp.)

(3) Polyethylene (Performalene PL manufactured by New Phase Technologies)

(4) Microcrystalline wax (Multiwax W-445 manufactured by Sonneborn, LLC)

(5) Candelilla wax (Refined Candelilla Wax Special manufactured by CERARICA NODA Co., Ltd.)

(6) Trimethylsiloxysilicic acid (X-21-5595 manufactured by Shin-Etsu Chemical Co., Ltd.)

(7) Isododecane (X-21-5595 manufactured by Shin-Etsu Chemical Co., Ltd.)

(8) Iron oxide black (Tarox BL-100 manufactured by Titan Kogyo, Ltd.)

(9) Talc (Talc JA-13R manufactured by Asada Milling Co., Ltd.)

(10) Nylon-12 (ORGASOL 2002 manufactured by Arkema K.K.)

The components (6) and (7) are sold as a premixed product (X-21-5595 manufactured by Shin-Etsu Chemical Co., Ltd.).

As shown in FIG. 6, the dextrin fatty acid esters of Examples 1, 3, and 4 and Comparative Examples 2, 3, and 7 to 9 were respectively used as the component (1) in Examples A1 to A3 and Comparative Examples A1 to A5.

The components (1) and (2) were heated and mixed, and the components (3) to (10) were added thereto, followed by mixing. A container was filled with the mixture to obtain eight evaluation samples (mascaras).

Usability tests by 10 study participants were conducted. For evaluation, the study participants assigned each sample a score with 5 representing excellent, 4 representing good, 3 representing fair, 2 representing poor, and 1 representing very poor. As for the average score of the 10 study participants, 4.0 or higher and 5.0 or lower was indicated by a double circle, 3.0 or higher and lower than 4.0 was indicated by a circle, 2.0 or higher and lower than 3.0 was indicated by a triangle, and 1.0 or higher and lower than 2.0 was indicated by an x-mark.

Evaluation Items (a) Preservation Stability

Each sample was left standing for 2 weeks in a thermostat of 50° C. Then, the appearance was visually observed. A state where oil separation was absent was given 5, a state where oil separation was slightly seen was given 4, a state where a small amount of an oil separated was given 3, a state where an oil separated considerably was given 2, and a state where an oil separated and made the sample difficult to use was given 1.

(b) Adhesion to brush: Moderate adhesion to a brush (c) Makeup effect/gloss: Beautiful makeup and good gloss were evaluated.

(d) Spread upon application: The ease of application was evaluated.

(e) Volume-up effect: The large amount of the mascara attached to eyelashes was evaluated.

(f) Separation effect: The ease of separation of every single eyelash was evaluated.

(g) Rub resistance: The absence of fading when the mascara was rubbed with tissue paper 1 hour after application was evaluated.

No oil separation was observed in the mascaras of Examples A1 to A3, and oil separation was slightly observed in Comparative Example A2. A small amount of an oil was observed to separate in Comparative Examples A3 to A5, and the mascara of Comparative Example A1 was difficult to use due to oil separation. The mascaras of Examples A1 to A3 scored high in the evaluation of adhesion to brush and separating properties because of an excellent restoring force. The mascaras of Comparative Examples A1 to A5 scored lower in the evaluation of adhesion to brush and separating properties than the mascaras of Examples A1 to A3. The mascaras of Examples A1 to A3 and Comparative Examples A1 to A3 scored high in the evaluation of rub resistance. The mascaras of Comparative Examples A4 and A5 scored low in the evaluation of rub resistance because the dextrin fatty acid ester itself was soft and isododecane left stickiness even after volatilization. The mascaras of Examples A1 to A3 were rated as a double circle for all of the items except that the mascara of Example A2 was rated as a circle for volume-up effect. Thus, the mascaras of Examples A1 to A3 had a high rating in comprehensive evaluation, as compared with the mascaras of Comparative Examples A1 to A5.

Example B

Cosmetic: body oil
Components
(1) Dextrin fatty acid ester
(2) Squalane
(3) Octyldodecyl myristate
(4) Isotridecyl isononanoate
(5) Cetyl ethylhexanoate
(6) Trioctanoin
(7) Tocopherol As shown in FIG. 7, the dextrin fatty acid esters of Examples 1, 3, and 4 and Comparative Examples 2, 3, and 7 to 9 were respectively used as the component (1) in Examples B1 to B3 and Comparative Examples B1 to B5.

The components (1) to (7) were dissolved by warming to obtain a body oil.

Usability tests by 10 study participants were conducted. An evaluation method was performed in the same way as in Example A.

Evaluation Items (a) Preservation stability: The same evaluation as in Example A was conducted.

(b) Absence of dropping: Ease of dropping from the hand when the cosmetic was taken out of the container was evaluated.

(c) Spread: Easy spreadability upon application was evaluated.

(d) Impression from use: The absence of stickiness and good texture were evaluated.

(e) Transparency: The absence of turbidity and white turbidity was evaluated.

The body oils of Examples B1 to B3 were rated as a double circle for all of the items. The body oils of Comparative Examples B1 to B5 had a lower rating in comprehensive evaluation than that of the body oils of Examples B1 to B3, though rated as a double circle for some items.

Example C

Cosmetic: cleansing gel
Components (% by weight)
(1) Dextrin fatty acid ester
(2) Mineral oil
(3) Isotridecyl isononanoate
(4) Squalane
(5) Octyldodecanol
(6) Trioctanoin
(7) Sorbeth-40 tetraoleate (UNIOX ST-40E manufactured by NOF Corp.)

(8) Water

As shown in FIG. 8, the dextrin fatty acid esters of Examples 1, 3, and 4 and Comparative Examples 2, 3, and 7 to 9 were respectively used as the component (1) in Examples C1 to C3 and Comparative Examples C1 to C5.

The components (1) to (7) were dissolved by warming. To the solution, the component (8) was added in small portions with stirring. The mixture was further cooled to room temperature with stirring to obtain a cleansing gel.

Usability tests by 10 study participants were conducted. An evaluation method was performed in the same way as in Example A.

Evaluation Items (a) Preservation stability: The same evaluation as in Example A was conducted.

(b) Transparency: The absence of turbidity and white turbidity was evaluated.

(c) Absence of dropping: Ease of dropping from the hand when the cosmetic was taken out of the container was evaluated.

(d) Spread: Whether to uniformly and easily spread the cosmetic for cleansing was evaluated.

(e) Impression from use: The absence of stickiness and good texture were evaluated.

The cleansing gels of Examples C1 to C3 were rated as a double circle for all of the items. The cleansing gels of Comparative Examples C1 to C5 had a lower rating in comprehensive evaluation than that of the cleansing gels of Examples C1 to C3, though rated as a double circle for some items.

Example D

Cosmetic: hair treatment gel
Components
(1) Dextrin fatty acid ester
(2) Olefin oligomer (NEXBASE 2004FG manufactured by Nisshin Oillio Group, Ltd.)
(3) Isononyl isononanoate
(4) Octyldodecanol
(5) Di(phytosteryl/octyldodecyl) lauroyl glutamate (EL-DEW PS-203 manufactured by Ajinomoto Co., Inc.)
(6) Isostearoyl hydrolyzed silk, isostearic acid (Promois EF-118 IS manufactured by Seiwa Kasei, Inc.)

As shown in FIG. 9, the dextrin fatty acid esters of Examples 1, 3, and 4 and Comparative Examples 2, 3, and 7 to 9 were respectively used as the component (1) in Examples D1 to D3 and Comparative Examples D1 to D5.

The components (1) to (6) were dissolved by warming to obtain a hair treatment gel.

Usability tests by 10 study participants were conducted. An evaluation method was performed in the same way as in Example A.

Evaluation Items (a) Preservation stability: The same evaluation as in Example A was conducted.

(b) Transparency: The absence of turbidity and white turbidity was evaluated.

(c) Absence of dropping: Ease of dropping from the hand when the cosmetic was taken out of the container was evaluated.

(d) Spread: Whether to spread uniformly and easily the cosmetic upon application was evaluated.

(e) Impression from use: The absence of stickiness and good texture were evaluated.

The hair treatment gels of Examples D1 to D3 were rated as a double circle for all of the items except for a circle for transparency. The hair treatment gels of Comparative Examples D1 to D5 were rated as a circle, a triangle, or an x-mark and had a lower rating in comprehensive evaluation than that of the hair treatment gels of Examples D1 to D3.

Example E

Cosmetic: lip color
Components
(1) Dextrin fatty acid ester
(2) Trioctanoin
(3) Dimethicone copolyol (KF-6017 manufactured by Shin-Etsu Chemical Co., Ltd.)
(4) Cyclomethicone
(5) Butylene glycol
(6) Water
(7) Pigment As shown in FIG. 10, the dextrin fatty acid esters of Examples 1, 3, and 4 and Comparative Examples 2, 3, and 7 to 9 were respectively used as the component (1) in Examples E1 to E3 and Comparative Examples E1 to E5.

The component (7) was dispersed in a portion of the component (2), and the component (1), the remaining amount of the component (2), and the components (3) and (4) were dissolved by warming. To the dispersion of the component (7) in the component (2), the mixture of the components (1) to (4) was added by stirring, followed by uniform mixing and dispersion. Subsequently, the components (5) and (6) were dissolved by warming and added to the mixture and dispersion of the components (1) to (4) at 80° C. for emulsification. The emulsion was cooled to obtain a lip color.

Usability tests by 10 study participants were conducted. An evaluation method was performed in the same way as in Example A.

Evaluation Items (a) Preservation stability: The same evaluation as in Example A was conducted.

(b) Ease to take out using applicator: Whether to easily take out the cosmetic using an applicator such as a brush was evaluated.

(c) Spread upon use: Good spreadability over the lip was evaluated.

(d) Smudge resistance: The state of smudge after a lapse of 3 hours after application was evaluated.

The lip colors of Examples E1 to E3 were rated as a double circle for all of the items. The lip colors of Comparative Examples E1 to E5 were rated as a circle, a triangle, or an x-mark for all of the items except that the lip color of Comparative Example E1 was rated as a double circle for preservation stability. Thus, the lip colors of Comparative Examples E1 to E5 had a lower rating in comprehensive evaluation than that of the lip colors of Examples E1 to E3.

Example F

Cosmetic: lip gloss
Components
(1) Dextrin fatty acid ester
(2) Mineral oil
(3) Pentaerythrityl hydrogenated rosinate, octyldodecyl isostearate (GEL-ISOD manufactured by Shin-Ei Chemical Co., Ltd.)
(4) Diisostearyl malate
(5) Diphenylsiloxy phenyl trimethicone (KF-56A manufactured by Shin-Etsu Chemical Co., Ltd.)

(6) Hydrogenated polyisobutene (Parleam manufactured by NOF Corp.)

(7) Pigment

As shown in FIG. 11, the dextrin fatty acid esters of Examples 1, 3, and 4 and Comparative Examples 2, 3, and 7 to 9 were respectively used as the component (1) in Examples F1 to F3 and Comparative Examples F1 to F5.

The components (1) to (5) were dissolved by warming. The component (6) was further added thereto, and the mixture is dissolved by warming. To the solution, the component (7) was added, warmed, and uniformly dispersed. Then, the dispersion was cooled to obtain a lip gloss.

Usability tests by 10 study participants were conducted. An evaluation method was performed in the same way as in Example A.

Evaluation Items (a) Preservation stability: The same evaluation as in Example A was conducted.

(b) Ease to take out using applicator: Whether to easily take out the cosmetic using an applicator such as a brush was evaluated.

(c) Spread upon use: Good spreadability over the lip was evaluated.

(d) Smudge resistance: The state of smudge after a lapse of 3 hours after application was evaluated.

The lip glosses of Examples F1 to F3 were rated as a double circle for all of the items. The lip glosses of Comparative Examples F1 to F5 were rated as a circle or a triangle for all of the evaluation items and had a lower rating in comprehensive evaluation than that of the lip glosses of Examples F1 to F3.

Example G

Cosmetic: oil foundation
Components (% by weight)
(1) Dextrin fatty acid ester
(2) Mineral oil
(3) Isotridecyl isononanoate
(4) Squalane
(5) Diphenylsiloxy phenyl trimethicone (KF-56A manufactured by Shin-Etsu Chemical Co., Ltd.)
(6) Isododecane (Permethyl 99A manufactured by Presperse Corp.)
(7) Pigment As shown in FIG. 12, the dextrin fatty acid esters of Examples 1, 3, and 4 and Comparative Examples 2, 3, and 7 to 9 were respectively used as the component (1) in Examples G1 to G3 and Comparative Examples G1 to G5.

The components (1) to (5) were dissolved by warming. The component (7) was further added thereto and uniformly dispersed. While this dispersion was cooled, the component (6) was added thereto at 50° C. The mixture was cooled to obtain an oil foundation.

Usability tests by 10 study participants were conducted. An evaluation method was performed in the same way as in Example A.

Evaluation Items (a) Preservation stability: The same evaluation as in Example A was conducted.

(b) Absence of dropping: Ease of dropping from the hand when the cosmetic was taken out of the container was evaluated.

(c) Long-lasting look: The cosmetic film after 3 hours was evaluated for long lasting look and a little deterioration.

(d) Impression from use: The absence of stickiness was evaluated.

The oil foundations of Examples G1 to G3 were rated as a double circle for all of the items. The oil foundations of Comparative Examples G1 to G5 were rated as a circle, a triangle, or an x-mark for all of the items except that the oil foundations of Comparative Examples G1 and G2 were rated as a double circle for long-lasting look. Thus, the oil foundations of Comparative Examples G1 to G5 had a lower rating in comprehensive evaluation than that of the oil foundations of Examples G1 to G3.

Example H

Cosmetic: beauty oil
Components
(1) Dextrin fatty acid ester
(2) Coix lacryma-jobi ma-yuen seed oil
(3) Isotridecyl isononanoate
(4) Jojoba oil
(5) Trioctanoin
(6) Mineral oil
(7) Squalane
(8) Olive oil
(9) Avocado oil
(10) Tocopherol As shown in FIG. 13, the dextrin fatty acid esters of Examples 1, 3, and 4 and Comparative Examples 2, 3, and 7 to 9 were respectively used as the component (1) in Examples H1 to G3 and Comparative Examples H1 to H5.

The components (1) to (10) were dissolved by warming to obtain a beauty oil.

Usability tests by 10 study participants were conducted. An evaluation method was performed in the same way as in Example A.

Evaluation Items (a) Preservation stability: The same evaluation as in Example A was conducted.

(b) Transparency: The absence of turbidity and white turbidity was evaluated.

(c) Absence of dropping: Ease of dropping from the hand when the cosmetic was taken out of the container was evaluated.

(d) Spread: Whether to uniformly and easily spread the cosmetic upon use was evaluated.

(e) Impression from use: The absence of stickiness and good texture were evaluated.

The beauty oils of Examples H1 to H3 were rated as a double circle for all of the items except for a circle for transparency. In this respect, the transparency was reduced due to the materials including plant oils such as olive oil and avocado oil and did not impair the functions of the beauty oils by any means. The beauty oils of Comparative Examples H1 to H5 were rated as a circle, a triangle, or an x-mark for all of the items except that the beauty oil of Comparative Example H1 was rated as a double circle for preservation stability. Thus, the beauty oils of Comparative Examples H1 to H5 had a lower rating in comprehensive evaluation than that of the beauty oils of Examples H1 to H3.

Example J

Cosmetic: liquid rouge
Components
(1) Dextrin fatty acid ester
(2) Dextrin isostearate
(3) Diisostearyl malate
(4) Isododecane (manufactured by Permethyl 99A Presperse Corp.)

(5) Hydrogenated polyisobutene (Parleam manufactured by NOF Corp.)

(6) Silica (Sunsphere L-51 AGC manufactured by AGC Si-Tech Co., Ltd.)

(7) Mica (Mica SA-350 manufactured by Yamaguchi Mica Co., Ltd.)

(8) Pearl agent (9) Pigment

As shown in FIG. 14, the dextrin fatty acid esters of Examples 1, 3, and 4 and Comparative Examples 2, 3, and 7 to 9 were respectively used as the component (1) in Examples J1 to J3 and Comparative Examples J1 to J5.

The components (1) to (10) were dissolved by warming to obtain a liquid rouge.

Usability tests by 10 study participants were conducted. An evaluation method was performed in the same way as in Example A.

Evaluation Items (a) Preservation stability: The same evaluation as in Example A was conducted.

(b) Ease to take out using applicator: Whether to easily take out the cosmetic using an applicator such as a brush was evaluated.

(c) Ease of application: Quick fitting to the lip and smooth application were evaluated.

(d) Smudge resistance: The state of smudge after a lapse of 3 hours after application was evaluated.

The liquid rouges of Examples J1 to J3 were rated as a double circle for all of the items. The liquid rouges of Comparative Examples J1 to J5 were rated as a circle, a triangle, or an x-mark for all of the items except that the liquid rouge of Comparative Example J1 was rated as a double circle for preservation stability. Thus, the liquid rouges of Comparative Examples J1 to J5 had a lower rating in comprehensive evaluation than that of the liquid rouges of Examples J1 to J3.

Example K

Cosmetic: gel eyeliner

Components (1) Dextrin fatty acid ester (2) Polyethylene (Performalene PL manufactured by New Phase Technologies)

(3) Microcrystalline wax (Multiwax W-445 manufactured by Sonneborn, LLC)

(4) Light liquid isoparaffin (IP Solvent 1620 manufactured by Idemitsu Petrochemical Co., Ltd.)

(5) Decamethylcyclopentasiloxane (6) Polymethylsilsesquioxane (KMP-590 manufactured by Shin-Etsu Chemical Co., Ltd.)

(7) Trimethylsiloxysilicic acid (X-21-5595 manufactured by Shin-Etsu Chemical Co., Ltd.)

(8) Isododecane (manufactured by Permethyl 99A Presperse Corp.)

(9) Pigment

As shown in FIG. 15, the dextrin fatty acid esters of Examples 1, 3, and 4 and Comparative Examples 2, 3, and 7 to 9 were respectively used as the component (1) in Examples K1 to K3 and Comparative Examples K1 to K5.

The components (1) to (4) were dissolved by warming. To the solution, the components (5) to (9) were added, warmed, and uniformly dispersed. Then, the dispersion was cooled to obtain a gel eyeliner.

Usability tests by 10 study participants were conducted. An evaluation method was performed in the same way as in Example A.

Evaluation Items (a) Preservation stability: The same evaluation as in Example A was conducted.

(b) Absence of dropping: Ease of dropping from the hand when the cosmetic was taken out of the container was evaluated.

(c) Spread upon use: Spreadability over the eyelids upon use was evaluated.

(d) Smudge resistance: The state of smudge after a lapse of 3 hours after application was evaluated.

The gel eyeliners of Examples K1 to K3 were rated as a double circle for all of the items. The gel eyeliners of Comparative Examples K1 to K5 were rated as a circle, a triangle, or an x-mark for all of the items except that the gel eyeliner of Comparative Example K1 was rated as a double circle for preservation stability. Thus, the gel eyeliners of Comparative Examples K1 to K5 had a lower rating in comprehensive evaluation than that of the gel eyeliners of Examples K1 to K3.

As described above, the present embodiment provides the following advantages.

(1) The dextrin in the dextrin fatty acid ester has an average degree of glycopolymerization of 3 or more and 100 or less, whereby the incapability of obtaining a soft gel is prevented while excessive reduction in the solubility of the dextrin fatty acid ester in an oil is also prevented. The linear saturated fatty acid bonded to the dextrin has 14 or more and 18 or less carbon atoms, whereby the restoring force imparted to cosmetics is enhanced. The branched saturated fatty acid has 14 or more and 18 or less carbon atoms, whereby the reaction efficiency between the dextrin and the fatty acid is improved while adequate viscosity properties are imparted to an oil. The molar fraction of the linear saturated fatty acid in the fatty acid is 0.75 or more and 0.95 or less, whereby a gelled oil has a smooth state while the restoring force is improved. The average degree of substitution of the fatty acid per glucose unit is 1.5 or more and 2.0 or less, whereby the syneresis properties are reduced.

A cosmetic containing this dextrin fatty acid ester has both of an excellent restoring force and low syneresis properties and therefore reduces its viscosity by the application of a force in order to take out the cosmetic from a preservation container containing the cosmetic. Therefore, the cosmetic, even if highly viscous, is easily taken out thereof. Also, the cosmetic resists flowing down when taken up on the palm or put on the face or the body. Furthermore, preservation stability is improved because syneresis is suppressed during preservation. Moreover, cosmetics, such as lip glosses or mascaras, for forming a cosmetic film on the skin, eyelashes, etc. reduce their viscosities by the application of a force and therefore spread well and are easy to apply. This facilitates uniform application of the cosmetics. At the completion of application of the cosmetics, the cosmetics restore their viscosities. Therefore, the cosmetics resist flowing down and thus easily maintain the cosmetic film state of completion of application.

(2) The average degree of glycopolymerization of the dextrin in the dextrin fatty acid ester is 3 or more and 50 or less, whereby a soft gel is obtained while the solubility of the dextrin fatty acid ester in an oil is enhanced.

(3) The molar fraction of the linear saturated fatty acid in the fatty acid of the dextrin fatty acid ester is in the range of 0.8 or more and 0.9 or less, and the average degree of substitution of the fatty acid per glucose unit is 1.65 or more and 1.80 or less, whereby the restoring force of an oil containing the dextrin fatty acid ester is improved while the syneresis properties is reduced.

(4) In the dextrin fatty acid ester, the linear saturated fatty acid is palmitic acid having 16 carbon atoms, and the branched saturated fatty acid is isopalmitic acid having 16 carbon atoms, whereby both of oil-gelling power and transparency are particularly excellent.

(5) The dextrin fatty acid ester having properties of conferring an excellent restoring force imparts a restoring force to a volatile hydrocarbon oil having a low viscosity even if its content is small with respect to the volatile hydrocarbon oil. Therefore, the dextrin fatty acid ester particularly exerts effects in such a way that the degree of freedom of cosmetic formulation is enhanced.

The invention claimed is:

1. A cosmetic comprising:
   an oil; and
   a gelling agent consisting of a dextrin fatty acid ester wherein
   the dextrin has an average degree of glycopolymerization of 3 or more and 100 or less,
   the fatty acid comprises one or more linear saturated fatty acids having 14 or more and 18 or less carbon atoms and one or more branched saturated fatty acids having 14 or more and 18 or less carbon atoms,
   a molar fraction of the linear saturated fatty acid in the fatty acid is 0.8 or more and 0.9 or less, and
   an average degree of substitution of the fatty acid per glucose unit is 1.61 or more and 1.80 or less,
   wherein the dextrin fatty acid ester is 3% by weight or more and 20% by weight or less of the cosmetic,
   wherein the oil has a content in the cosmetic greater than the dextrin fatty acid ester,
   wherein the cosmetic is a gelled cosmetic, and
   wherein the gelled cosmetic has a viscosity after cancellation of an applied force that is greater than or equal to 50 percent or more with respect to the viscosity immediately prior to application of the applied force within a period of time less than 20 seconds after the cancellation.

2. The cosmetic according to claim 1, wherein the oil comprises a volatile hydrocarbon oil.

3. The cosmetic according to claim 1, wherein the average degree of glycopolymerization of the dextrin is 3 or more and 50 or less.

4. The cosmetic according to claim 1, wherein the average degree of glycopolymerization of the dextrin is 3 or more and 20 or less.

5. The cosmetic according to claim 1, wherein the average degree of substitution of the fatty acid per glucose unit is 1.65 or more and 1.80 or less.

6. The cosmetic according to claim 1, wherein the linear saturated fatty acid is palmitic acid, and the branched saturated fatty acid is isopalmitic acid.

7. The cosmetic of claim 1, wherein the gelled cosmetic has a viscosity after cancellation of an applied force that is greater than or equal to 50 percent or more with respect to the viscosity immediately prior to application of the applied force within a period of time less than 10 seconds after the cancellation.

* * * * *